US010053512B2

(12) United States Patent
Sahin et al.

(10) Patent No.: US 10,053,512 B2
(45) Date of Patent: *Aug. 21, 2018

(54) ANTIBODIES AGAINST CLAUDIN 18.2 USEFUL IN CANCER DIAGNOSIS

(71) Applicants: Ganymed Pharmaceuticals AG, Mainz (DE); TRON—Translationale Onkologie an der Universitätsmedizin der Johannes Gutenberg-Universität Mainz gGmbH, Mainz (DE)

(72) Inventors: Ugur Sahin, Mainz (DE); Ozlem Tureci, Mainz (DE); Rita Mitnacht-Kraus, Friedberg (DE); Stefan Woll, Nackenheim (DE)

(73) Assignees: GANYMED PHARMACEUTICALS AG, Mainz (DE); TRON—TRANSLATIONALE ONKOLOGIE AN DER UNIVERSITATSMEDIZIN DER JOHANNES GUTENBERG—UNIVERSITAT MAINZ GEMEINNUTZIGE GMBH, Mainz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/227,565

(22) Filed: Aug. 3, 2016

(65) Prior Publication Data

US 2016/0333109 A1    Nov. 17, 2016

Related U.S. Application Data

(62) Division of application No. 14/397,244, filed as application No. PCT/EP2013/001331 on May 6, 2013, now Pat. No. 9,512,232.

(30) Foreign Application Priority Data

May 9, 2012    (EP) .................. PCT/EP2012/001991

(51) Int. Cl.
*A61K 49/00*     (2006.01)
*C07K 16/00*     (2006.01)
*C07K 16/18*     (2006.01)
*C07K 16/28*     (2006.01)
*C07K 16/30*     (2006.01)
*G01N 1/00*      (2006.01)
*G01N 33/574*    (2006.01)
*A61K 51/10*     (2006.01)

(52) U.S. Cl.
CPC .............. *C07K 16/30* (2013.01); *C07K 16/28* (2013.01); *C07K 16/303* (2013.01); *C07K 16/3023* (2013.01); *C07K 16/3046* (2013.01); *G01N 33/57492* (2013.01); *C07K 2317/34* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,790,824 A | 12/1988 | Morrow et al. |
| 4,881,175 A | 11/1989 | Ladner |
| 4,941,880 A | 7/1990 | Burns |
| 4,946,778 A | 8/1990 | Ladner et al. |
| 4,954,617 A | 9/1990 | Fanger et al. |
| 5,013,653 A | 5/1991 | Huston et al. |
| 5,064,413 A | 11/1991 | McKinnon, Jr. et al. |
| 5,091,513 A | 2/1992 | Huston et al. |
| 5,132,405 A | 7/1992 | Huston et al. |
| 5,258,498 A | 11/1993 | Huston et al. |
| 5,260,203 A | 11/1993 | Ladner et al. |
| 5,312,335 A | 5/1994 | McKinnon, Jr. et al. |
| 5,374,548 A | 12/1994 | Caras |
| 5,383,851 A | 1/1995 | McKinnon, Jr. et al. |
| 5,399,163 A | 3/1995 | Peterson et al. |
| 5,399,331 A | 3/1995 | Loughrey et al. |
| 5,416,016 A | 5/1995 | Low et al. |
| 5,455,030 A | 10/1995 | Ladner et al. |
| 5,476,786 A | 12/1995 | Huston |

(Continued)

FOREIGN PATENT DOCUMENTS

| | | |
|---|---|---|
| AU | 2003282101 | 7/2010 |
| CA | 2379661 | 9/2003 |

(Continued)

OTHER PUBLICATIONS

Padlan (Advances in Protein Chemistry, 1996, 49:57-133) reviewed.*
Berglund et al. (Protein Science, 2008, 17:606-613).*
Corada (Blood, 2001; 97:1679-84).*
Tzartos et al. (Methods in Molecular Biology, 1996, 66:55-66).*
Kulkarni-Kale et al. (Nucleic Acid Research, 2005, 33:W168-W171).*
Almagro & Fransson (Frontiers in Bioscience 2008; 13:1619-33).*
De Genst et al. (Developmental and Comparative Immunology, 2006, 30:187-198).*
Ward et al. (Nature, 1989, 341:544-546).*
Barthelemy et al. (Journal of Biological Chemistry, 2008, 283:3639-3654).*

(Continued)

*Primary Examiner* — Julie Wu
(74) *Attorney, Agent, or Firm* — Neal, Gerber & Eisenberg LLP; Kevin A. O'Connor

(57) ABSTRACT

The invention relates to antibodies directed against an epitope located within the C-terminal portion of CLDN18.2 which are useful, for example, in diagnosing cancer and/or in determining whether cancer cells express CLDN18.2.

34 Claims, 3 Drawing Sheets

(56) References Cited

U.S. PATENT DOCUMENTS

| | | |
|---|---|---|
| 5,482,858 A | 1/1996 | Huston et al. |
| 5,624,821 A | 4/1997 | Winter et al. |
| 5,648,260 A | 7/1997 | Winter et al. |
| 5,869,045 A | 2/1999 | Hellstrom et al. |
| 6,121,022 A | 9/2000 | Presta et al. |
| 6,194,551 B1 | 2/2001 | Idusogie et al. |
| 6,235,481 B1 | 5/2001 | Horikawa et al. |
| 6,277,375 B1 | 8/2001 | Ward |
| 6,380,362 B1 | 4/2002 | Watson et al. |
| 6,946,263 B2 | 9/2005 | Ferrara et al. |
| 6,951,920 B2 | 10/2005 | Gao et al. |
| 7,060,800 B2 | 6/2006 | Gorman |
| 7,071,304 B2 | 7/2006 | Eaton et al. |
| 7,074,912 B2 | 7/2006 | Eaton et al. |
| 7,098,312 B2 | 8/2006 | Baker et al. |
| 7,109,292 B2 | 9/2006 | Goddard et al. |
| 7,125,962 B2 | 10/2006 | Baker et al. |
| 7,153,939 B2 | 12/2006 | Goddard et al. |
| 7,189,563 B2 | 3/2007 | Eaton et al. |
| 7,189,821 B2 | 3/2007 | Goddard et al. |
| 7,193,059 B2 | 3/2007 | Goddard et al. |
| 7,193,074 B2 | 3/2007 | Goddard et al. |
| 7,196,166 B2 | 3/2007 | Goddard et al. |
| 7,196,167 B2 | 3/2007 | Goddard et al. |
| 7,202,335 B2 | 4/2007 | Goddard et al. |
| 7,211,645 B2 | 5/2007 | Goddard et al. |
| 7,223,841 B2 | 5/2007 | Goddard et al. |
| 7,232,889 B2 | 6/2007 | Goddard et al. |
| 7,241,872 B2 | 7/2007 | Goddard et al. |
| 7,253,256 B2 | 8/2007 | Goddard et al. |
| 7,271,247 B2 | 9/2007 | Goddard et al. |
| 7,309,769 B2 | 12/2007 | Goddard et al. |
| 7,317,093 B2 | 1/2008 | Goddard et al. |
| 7,319,008 B2 | 1/2008 | Goddard et al. |
| 7,339,024 B2 | 3/2008 | Goddard et al. |
| 7,339,034 B2 | 3/2008 | Goddard et al. |
| 7,351,543 B2 | 4/2008 | Goddard et al. |
| 7,351,804 B2 | 4/2008 | Goddard et al. |
| 7,368,531 B2 | 5/2008 | Rosen et al. |
| 7,375,184 B2 | 5/2008 | Goddard et al. |
| 7,399,834 B2 | 7/2008 | Botstein et al. |
| 7,405,268 B2 | 7/2008 | Goddard et al. |
| 7,411,051 B2 | 8/2008 | Rosen et al. |
| 7,423,120 B2 | 9/2008 | Goddard et al. |
| 7,425,605 B2 | 9/2008 | Goddard et al. |
| 7,427,668 B2 | 9/2008 | Gorman |
| 7,488,796 B2 | 2/2009 | Goddard et al. |
| 7,495,083 B2 | 2/2009 | Goddard et al. |
| 7,507,404 B2 | 3/2009 | Goddard et al. |
| 7,527,933 B2 | 5/2009 | Sahin et al. |
| 7,538,086 B2 | 5/2009 | Goddard et al. |
| 7,678,373 B2 * | 3/2010 | Desnoyers ............ C07K 16/22 424/145.1 |
| 7,696,317 B2 | 4/2010 | Gorman |
| 7,696,319 B2 | 4/2010 | Baker et al. |
| 7,893,211 B2 | 2/2011 | Gorman |
| 8,088,588 B2 | 1/2012 | Sahin et al. |
| 8,148,507 B2 | 4/2012 | Parham et al. |
| 8,168,427 B2 | 5/2012 | Sahin et al. |
| 8,425,902 B2 | 4/2013 | Sahin et al. |
| 8,426,573 B2 | 4/2013 | Parham et al. |
| 8,586,047 B2 | 11/2013 | Sahin et al. |
| 8,637,012 B2 | 1/2014 | Sahin et al. |
| 8,945,847 B2 | 2/2015 | Benvenisty et al. |
| 9,044,382 B2 | 6/2015 | Tureci |
| 9,329,189 B2 * | 5/2016 | Mercken ................ C07K 16/18 |
| 9,512,232 B2 * | 12/2016 | Sahin ..................... C07K 16/30 |
| 2002/0119130 A1 | 8/2002 | Eaton et al. |
| 2003/0008352 A1 | 1/2003 | Baker et al. |
| 2003/0008353 A1 | 1/2003 | Baker et al. |
| 2003/0017468 A1 | 1/2003 | Chen et al. |
| 2003/0017534 A1 | 1/2003 | Buelow et al. |
| 2003/0018172 A1 | 1/2003 | Eaton et al. |
| 2003/0022296 A1 | 1/2003 | Baker et al. |
| 2003/0022298 A1 | 1/2003 | Baker et al. |
| 2003/0022835 A1 | 1/2003 | Watson et al. |
| 2003/0027268 A1 | 2/2003 | Baker et al. |
| 2003/0027272 A1 | 2/2003 | Baker et al. |
| 2003/0027279 A1 | 2/2003 | Baker et al. |
| 2003/0027281 A1 | 2/2003 | Baker et al. |
| 2003/0032113 A1 | 2/2003 | Baker et al. |
| 2003/0032119 A1 | 2/2003 | Baker et al. |
| 2003/0036146 A1 | 2/2003 | Baker et al. |
| 2003/0038827 A1 | 2/2003 | Baker et al. |
| 2003/0040053 A1 | 2/2003 | Baker et al. |
| 2003/0040057 A1 | 2/2003 | Baker et al. |
| 2003/0040061 A1 | 2/2003 | Baker et al. |
| 2003/0040078 A1 | 2/2003 | Baker et al. |
| 2003/0040471 A1 | 2/2003 | Watson et al. |
| 2003/0044925 A1 | 3/2003 | Baker et al. |
| 2003/0049756 A1 | 3/2003 | Baker et al. |
| 2003/0054406 A1 | 3/2003 | Baker et al. |
| 2003/0054468 A1 | 3/2003 | Baker et al. |
| 2003/0060602 A1 | 3/2003 | Eaton et al. |
| 2003/0068682 A1 | 4/2003 | Baker et al. |
| 2003/0068684 A1 | 4/2003 | Baker et al. |
| 2003/0068726 A1 | 4/2003 | Baker et al. |
| 2003/0073129 A1 | 4/2003 | Baker et al. |
| 2003/0073821 A1 | 4/2003 | Eaton et al. |
| 2003/0082626 A1 | 5/2003 | Baker et al. |
| 2003/0083462 A1 | 5/2003 | Baker et al. |
| 2003/0096954 A1 | 5/2003 | Baker et al. |
| 2003/0100061 A1 | 5/2003 | Baker et al. |
| 2003/0109672 A1 | 6/2003 | Baker et al. |
| 2003/0113795 A1 | 6/2003 | Baker et al. |
| 2003/0118592 A1 | 6/2003 | Ledbetter et al. |
| 2003/0119097 A1 | 6/2003 | Baker et al. |
| 2003/0120053 A1 | 6/2003 | Baker et al. |
| 2003/0125535 A1 | 7/2003 | Baker et al. |
| 2003/0130483 A1 | 7/2003 | Eaton et al. |
| 2003/0133939 A1 | 7/2003 | Ledbetter et al. |
| 2003/0135034 A1 | 7/2003 | Baker et al. |
| 2003/0138882 A1 | 7/2003 | Eaton et al. |
| 2003/0152939 A1 | 8/2003 | Smithson et al. |
| 2003/0166104 A1 | 9/2003 | Baker et al. |
| 2003/0166114 A1 | 9/2003 | Baker et al. |
| 2003/0171550 A1 | 9/2003 | Eaton et al. |
| 2003/0180839 A1 | 9/2003 | Eaton et al. |
| 2003/0180840 A1 | 9/2003 | Eaton et al. |
| 2003/0180841 A1 | 9/2003 | Eaton et al. |
| 2003/0180842 A1 | 9/2003 | Eaton et al. |
| 2003/0180843 A1 | 9/2003 | Eaton et al. |
| 2003/0180844 A1 | 9/2003 | Eaton et al. |
| 2003/0180846 A1 | 9/2003 | Eaton et al. |
| 2003/0180848 A1 | 9/2003 | Eaton et al. |
| 2003/0180850 A1 | 9/2003 | Eaton et al. |
| 2003/0180853 A1 | 9/2003 | Eaton et al. |
| 2003/0180855 A1 | 9/2003 | Eaton et al. |
| 2003/0180856 A1 | 9/2003 | Eaton et al. |
| 2003/0180857 A1 | 9/2003 | Eaton et al. |
| 2003/0180858 A1 | 9/2003 | Eaton et al. |
| 2003/0180859 A1 | 9/2003 | Eaton et al. |
| 2003/0180862 A1 | 9/2003 | Eaton et al. |
| 2003/0180863 A1 | 9/2003 | Eaton et al. |
| 2003/0180904 A1 | 9/2003 | Eaton et al. |
| 2003/0180908 A1 | 9/2003 | Eaton et al. |
| 2003/0180909 A1 | 9/2003 | Eaton et al. |
| 2003/0180910 A1 | 9/2003 | Eaton et al. |
| 2003/0180912 A1 | 9/2003 | Eaton et al. |
| 2003/0180913 A1 | 9/2003 | Eaton et al. |
| 2003/0180914 A1 | 9/2003 | Eaton et al. |
| 2003/0180915 A1 | 9/2003 | Eaton et al. |
| 2003/0180916 A1 | 9/2003 | Eaton et al. |
| 2003/0180917 A1 | 9/2003 | Eaton et al. |
| 2003/0180918 A1 | 9/2003 | Eaton et al. |
| 2003/0180920 A1 | 9/2003 | Eaton et al. |
| 2003/0180921 A1 | 9/2003 | Eaton et al. |
| 2003/0180922 A1 | 9/2003 | Eaton et al. |
| 2003/0181637 A1 | 9/2003 | Eaton et al. |
| 2003/0181638 A1 | 9/2003 | Eaton et al. |
| 2003/0181641 A1 | 9/2003 | Eaton et al. |
| 2003/0181650 A1 | 9/2003 | Eaton et al. |
| 2003/0181652 A1 | 9/2003 | Eaton et al. |
| 2003/0181666 A1 | 9/2003 | Eaton et al. |

(56) References Cited

U.S. PATENT DOCUMENTS

| | | |
|---|---|---|
| 2003/0181675 A1 | 9/2003 | Eaton et al. |
| 2003/0181680 A1 | 9/2003 | Eaton et al. |
| 2003/0181697 A1 | 9/2003 | Eaton et al. |
| 2003/0181700 A1 | 9/2003 | Eaton et al. |
| 2003/0181701 A1 | 9/2003 | Eaton et al. |
| 2003/0181702 A1 | 9/2003 | Eaton et al. |
| 2003/0181703 A1 | 9/2003 | Eaton et al. |
| 2003/0186318 A1 | 10/2003 | Baker et al. |
| 2003/0186407 A1 | 10/2003 | Baker et al. |
| 2003/0187189 A1 | 10/2003 | Baker et al. |
| 2003/0187195 A1 | 10/2003 | Baker et al. |
| 2003/0187196 A1 | 10/2003 | Eaton et al. |
| 2003/0187239 A1 | 10/2003 | Baker et al. |
| 2003/0187242 A1 | 10/2003 | Eaton et al. |
| 2003/0190669 A1 | 10/2003 | Eaton et al. |
| 2003/0190698 A1 | 10/2003 | Eaton et al. |
| 2003/0191290 A1 | 10/2003 | Eaton et al. |
| 2003/0195347 A1 | 10/2003 | Baker et al. |
| 2003/0206188 A1 | 11/2003 | Baker et al. |
| 2003/0211574 A1 | 11/2003 | Baker et al. |
| 2004/0010134 A1 | 1/2004 | Rosen et al. |
| 2004/0018969 A1 | 1/2004 | Rosen et al. |
| 2004/0058411 A1 | 3/2004 | Eaton et al. |
| 2005/0026211 A1 | 2/2005 | Chen et al. |
| 2005/0181375 A1 | 8/2005 | Aziz et al. |
| 2005/0196832 A1 | 9/2005 | Goddard et al. |
| 2005/0202526 A1 | 9/2005 | Baker et al. |
| 2006/0035852 A1 | 2/2006 | Sahin et al. |
| 2006/0073544 A1 | 4/2006 | Baker et al. |
| 2006/0073545 A1 | 4/2006 | Baker et al. |
| 2006/0084794 A1 | 4/2006 | Rosen et al. |
| 2007/0065859 A1 | 3/2007 | Wang et al. |
| 2007/0072175 A1 | 3/2007 | Cooper et al. |
| 2007/0099251 A1 | 5/2007 | Zhang et al. |
| 2007/0099833 A1 | 5/2007 | Rosen et al. |
| 2007/0224663 A1 | 9/2007 | Rosen et al. |
| 2008/0050726 A1 | 2/2008 | Wang et al. |
| 2008/0166350 A1 | 7/2008 | Tuereci et al. |
| 2008/0286821 A1 | 11/2008 | Eaton et al. |
| 2009/0018031 A1 | 1/2009 | Trinklein et al. |
| 2009/0197301 A1 | 8/2009 | Baker et al. |
| 2010/0021886 A1 | 1/2010 | Wang et al. |
| 2010/0286048 A1 | 11/2010 | Rosen et al. |
| 2011/0190380 A1 | 8/2011 | Feinstein et al. |
| 2012/0164160 A1 | 6/2012 | Sahin et al. |
| 2012/0195830 A1 | 8/2012 | Sahin et al. |
| 2014/0073524 A1 | 3/2014 | Hood et al. |

FOREIGN PATENT DOCUMENTS

| | | |
|---|---|---|
| CN | 101584860 | 11/2009 |
| DE | 10254601 | 6/2004 |
| DE | 10354601 | 6/2005 |
| DE | 112005002742 | 8/2007 |
| EP | 0338841 | 10/1989 |
| EP | 1430902 | 6/2004 |
| EP | 1790664 | 5/2007 |
| EP | 1948693 | 7/2008 |
| EP | 1983002 | 10/2008 |
| EP | 1997832 | 12/2008 |
| EP | 2036987 | 3/2009 |
| EP | 2145902 | 9/2010 |
| EP | 2311879 | 4/2011 |
| EP | 2295469 | 5/2011 |
| EP | 2311877 | 5/2011 |
| EP | 2311878 | 5/2011 |
| EP | 2325210 | 5/2011 |
| EP | 2371848 | 5/2011 |
| EP | 2366709 | 9/2011 |
| EP | 2371849 | 10/2011 |
| EP | 2380903 | 10/2011 |
| EP | 2383288 | 11/2011 |
| EP | 2392593 | 12/2011 |
| EP | 2402758 | 1/2012 |
| EP | 2481814 | 8/2012 |
| EP | 2664676 | 11/2013 |
| FR | 2876705 | 4/2006 |
| JP | 2000032984 | 2/2000 |
| JP | 2002524103 | 8/2002 |
| JP | 2003000249 | 7/2003 |
| JP | 2004520814 | 7/2004 |
| KR | 20050083962 | 8/2005 |
| WO | WO1987004462 | 7/1987 |
| WO | WO1988000052 | 1/1988 |
| WO | WO1989001036 | 2/1989 |
| WO | WO1992004381 | 3/1992 |
| WO | WO1994010332 | 5/1994 |
| WO | WO1996002552 | 2/1996 |
| WO | WO1996033265 | 10/1996 |
| WO | WO1996033739 | 10/1996 |
| WO | WO1997025426 | 7/1997 |
| WO | WO1999045962 | 9/1999 |
| WO | WO1999064452 | 12/1999 |
| WO | WO2000008206 | 2/2000 |
| WO | WO2000012708 | 3/2000 |
| WO | WO2000015659 | 3/2000 |
| WO | WO2000015796 | 3/2000 |
| WO | WO2000020447 | 4/2000 |
| WO | WO2000023603 | 4/2000 |
| WO | WO2000058473 | 5/2000 |
| WO | WO2000053756 | 9/2000 |
| WO | WO2000053757 | 9/2000 |
| WO | WO2000056889 | 9/2000 |
| WO | WO2000073348 | 12/2000 |
| WO | WO2000073454 | 12/2000 |
| WO | WO2000075316 | 12/2000 |
| WO | WO2000075327 | 12/2000 |
| WO | WO2000077037 | 12/2000 |
| WO | WO2000078961 | 12/2000 |
| WO | WO2001004311 | 1/2001 |
| WO | WO2001016318 | 3/2001 |
| WO | WO2001027257 | 4/2001 |
| WO | WO2001040466 | 6/2001 |
| WO | WO2001048192 | 7/2001 |
| WO | WO2001049715 | 7/2001 |
| WO | WO2001054708 | 8/2001 |
| WO | WO2001055314 | 8/2001 |
| WO | WO2001055318 | 8/2001 |
| WO | WO2001055326 | 8/2001 |
| WO | WO2001055367 | 8/2001 |
| WO | WO2001062920 | 8/2001 |
| WO | WO2001068848 | 9/2001 |
| WO | WO2001070979 | 9/2001 |
| WO | WO2001075067 | 10/2001 |
| WO | WO2001077137 | 10/2001 |
| WO | WO2001090357 | 11/2001 |
| WO | WO2002002621 | 1/2002 |
| WO | WO2002014500 | 2/2002 |
| WO | WO2002018576 | 3/2002 |
| WO | WO2002020569 | 3/2002 |
| WO | WO2002022885 | 3/2002 |
| WO | WO2002043478 | 6/2002 |
| WO | WO2002061087 | 8/2002 |
| WO | WO2002066682 | 8/2002 |
| WO | WO2002068579 | 9/2002 |
| WO | WO2002068600 | 9/2002 |
| WO | WO2002103028 | 12/2002 |
| WO | WO2003004604 | 1/2003 |
| WO | WO2003014303 | 2/2003 |
| WO | WO2003101283 | 12/2003 |
| WO | WO2004029207 | 4/2004 |
| WO | WO2004035607 | 4/2004 |
| WO | WO2004045535 | 6/2004 |
| WO | WO2004047863 | 6/2004 |
| WO | WO2004063351 | 7/2004 |
| WO | WO2004063355 | 7/2004 |
| WO | WO2004074455 | 9/2004 |
| WO | WO2005005601 | 1/2005 |
| WO | WO2005032495 | 4/2005 |
| WO | WO2005052182 | 6/2005 |
| WO | WO2005061548 | 7/2005 |
| WO | WO2005076939 | 8/2005 |
| WO | WO2005082398 | 9/2005 |
| WO | WO2005111198 | 11/2005 |

(56) References Cited

FOREIGN PATENT DOCUMENTS

| WO | WO2005113587 | 12/2005 |
|---|---|---|
| WO | WO2005114221 | 12/2005 |
| WO | WO2006023121 | 3/2006 |
| WO | WO2006024283 | 3/2006 |
| WO | WO2006042995 | 4/2006 |
| WO | WO2007018843 | 2/2007 |
| WO | WO2007021423 | 2/2007 |
| WO | WO2007027867 | 3/2007 |
| WO | WO2007035676 | 3/2007 |
| WO | WO2007035690 | 3/2007 |
| WO | WO2007047796 | 4/2007 |
| WO | WO2007059997 | 5/2007 |
| WO | WO2007115045 | 10/2007 |
| WO | WO2008013948 | 1/2008 |
| WO | WO2008013954 | 1/2008 |
| WO | WO2008021115 | 2/2008 |
| WO | WO2008021290 | 2/2008 |
| WO | WO2008043561 | 4/2008 |
| WO | WO2008073919 | 6/2008 |
| WO | WO2008082730 | 7/2008 |
| WO | WO2008095152 | 8/2008 |
| WO | WO2008145338 | 12/2008 |
| WO | WO2008154333 | 12/2008 |
| WO | WO2009015050 | 1/2009 |
| WO | WO2009035497 | 3/2009 |
| WO | WO2009037090 | 3/2009 |
| WO | WO2009047362 | 4/2009 |
| WO | WO2009102367 | 8/2009 |
| WO | WO2009148593 | 12/2009 |
| WO | WO2009155609 | 12/2009 |
| WO | WO2010045889 | 4/2010 |
| WO | WO2010059543 | 5/2010 |
| WO | WO2010108638 | 9/2010 |
| WO | WO2010120526 | 10/2010 |
| WO | WO2011038461 | 4/2011 |
| WO | WO2011068839 | 6/2011 |
| WO | WO2011113546 | 9/2011 |
| WO | WO2011154139 | 12/2011 |
| WO | WO2011163267 | 12/2011 |
| WO | WO2012070014 | 5/2012 |
| WO | WO2012096272 | 7/2012 |
| WO | WO2012120026 | 9/2012 |
| WO | WO2013151672 | 10/2013 |
| WO | WO2013167153 | 11/2013 |
| WO | WO2013167259 | 11/2013 |
| WO | WO2013174403 | 11/2013 |
| WO | WO2013174404 | 11/2013 |
| WO | WO2013174509 | 11/2013 |
| WO | WO2013174510 | 11/2013 |
| WO | WO2014025198 | 2/2014 |
| WO | WO2014025199 | 2/2014 |
| WO | WO2014031859 | 2/2014 |
| WO | WO2014039893 | 3/2014 |

OTHER PUBLICATIONS

Choi et al. (Molecular BioSystems, 2011, 7:3327-334).*
Griffiths et al. (The EMBO Journal, 1993, 12:725-734).*
Klimka et al. (British Journal of Cancer, 2000, 83:252-260).*
Beiboer et al. (Journal of Molecular Biology, 2000, 296:833-849).*
Abaza et al (Journal of Protein Chemistry, vol. 11, No. 5, 1992, pp. 433-444).
Adams et al, Science (1991) 252:1651 (http://www.ncbi.nlm.nih.gov/BLAST).
Advisory Action for U.S. Appl. No. 12/601,488, dated Jun. 26, 2012.
Al-Agha et al., Arch. Pathol. Lab. Med. 130:1725-1730 (2006).
Altman et al., Science (1996) 274:94-96.
Amon et al., "Monoclonal Antibodies for Immunotargeting of Drugs in Cancer Therapy", in Monoclonal Antibodies and Cancer Therapy, 1985.
Anderson et al., J. Immunol. (1989) 143:1899-1904.
Appella et al., Biomed Pept Proteins Nucleic Acids (1995) 1:177-84.
Azorsa et al., J. Immunol. Methods (1999) 229: 35-48.
Baldwin et al. (eds) pp. 303-316 (Academic Press 1985).
Baranova et al., In Silico Screening for Tumour-Specific Expressed Sequences in Human Genome, FEBS Letters (2001) 508:143-148.
Basic Local Alignment Search Tool (BLAST), NCBI Blast: Nucleoride Sequence (786 letters). http://blast/ncbi/nlm.nih.gov/Blast.cgi dated Mar. 6, 2010 (4 pages).
Basic Local Alignment Search Tool (BLAST), NCBI Blast: Nucleoride Sequence (180 letters). http://blast/ncbi/nlm.nih.gov/Blast.cgi dated Mar. 6, 2010 (4 pages).
Benedict et al (J. Exp. Medicine, 2001, 193(1) 89-99).
Bennett et al., Nature (1998) 393:478.
Benny K.C. Lo Antibody Engineering ISBN 1-58829-092-1, 2003.
Benny K.C. Lo Antibody Engineering ISBN 1-58829-092-1, 2004.
Berge, S. M., et al. (1977) J. Pharm. Sci. 66:1-19.
Berzofsky et al., "Antibody-Antigen Interactions" In Fundamental Immunology, Paul, W. E., Ed., Raven Press New York, N Y (1984).
Bindon et al., 1988, Eur. J. Immunol. 18:1507-1514.
Bingle et al., Biochem. Biophys. Acta. (2000) 1493:363-7.
Bird et al., "Single-Chain Antigen-Binding Proteins," Science 242: 423-426 (1988).
Bloeman, P.G. et al. (1995) FEBS Lett. 357: 140.
Brandlein et al., "PAM-1, a natural human IgM antibody as new tool for detection of breast and prostate precursors", Human Antibodies, IOS Press, Amsterdam, NL, vol. 13, No. 4, Jan. 1, 2004 (Jan. 1, 2004), pp. 97-104.
Brennan et al., Science (1985) 229: 81-83.
Brennan et al., J. Autoimmunity (1989) 2 (suppl.): 177-186.
Briscoe et al. (1995) Am. J. Physiol. 1233:134.
Büchler, P. et al: "Therapy for pancreatic cancer with a recombinant humanized anti-HER2 antibody (herceptin)", Journal of Gastrointestinal Surgery, Bd. 5, Nr. 2, Apr. 1, 2001 (Apr. 1, 2001), Seiten 139-146.
Burgess et al (J of Cell Bio. 111 :2129-2138, 1990).
Buskens, C. et al., Digestive Disease Week Abstracts and Itinerary Planner (2003) abstract No. 850.
Chomczynski & Sacchi, Anal. Biochem. (1987) 162:156-9.
Clark, W.R., The Experimental Foundations of Modern Immunology (1986) Wiley & Sons, Inc., New York.
Coleman et al (Research in Immunology, 1994; 145(1): 33-36).
Cragg et al., 2003, Blood 101:1045-10523.
Cunningham-Rundles et al. (1992) Biological activities of polyethylene-glycoll. Immunoglobulin conjugates. Resistance to enzymatic degradation J. Immunol. Methods, 152: 177-190.
Current Protocols in Protein Science, John Wiley & Sons Ltd., Wiley InterScience, 2010.
Dabbs, J., MD, Diagnostic Immunohistochemistry (2001) ISBN: 0443065667.
Database Genbank, Sequence having accession No. AF221069, Oct. 10, 2001.
De Wildt et al, J. Immunol. Methods (1997) 207: 61-67.
Dillman, Monoclonal Antibodies for Treating Cancer, Annals of Internal Medicine, 1989, 111:592-603.
Drexler et al, Leukemia and Lymphoma (1993) 9:1-25.
Dunbar et al., Curr. Biol. (1998) 8:413-416.
Durand et al., Clinical Chemistry (2000) 46:795-805.
EMBL:AK025111, http://ibis/exam/dbfetch.jsp?id=EMBL%3AAK02511 (2 pages), Oct. 7, 2008.
Embleton et al., Immunol. Ser. (1984) 23:181-207.
Engberg, J., et al., Recombinant antibodies with the antigen-specific, MHC restricted specificity of T cells: novel reagents for basic and clinical investigations and immunotherapy, Immunotechnology (1999) 4:273-278.
European Search Report for patent application No. 11 00 7306, dated Feb. 28, 2012.
European Search Report for patent application No. 11 00 7308.7, dated Nov. 7, 2012.
European Search Report for patent application No. 11 00 7310.3, dated Jun. 27, 2012.
European Search Report for patent application No. 11 00 7311.1, dated Jun. 27, 2012.
European Search Report for patent application No. 11 00 7313.7, dated Jun. 29, 2012.

(56) References Cited

OTHER PUBLICATIONS

European Search Report for patent application No. 11 00 7317.8, dated Jun. 25, 2012.
European Search Report for patent application No. 11 00 7326.9, dated Mar. 19, 2012.
Examiner's report No. 2 on Australian patent application No. 20003282101 of Sep. 4, 2009.
Final Office Action dated Jan. 18, 2012 in U.S. Appl. No. 12/423,153.
Fischer, R., et al. (1999) Biol. Chem. 380: 825-839.
Fu et al., Embo J. (1996) 15:4392-4401.
Gajewski et al., J. Immunol. (1995) 154:5637-5648.
Gardsvoll, J. Immunol. Methods (2000) 234:107-116.
Glennie et al., J. Immunol. (1987) 139:2367-2375.
Goodman and Gilman, "The Pharmacological Basis of Therapeutics", 8th Edition, 1990, McGraw-Hill, Inc., in particular Chapter 52 (Antineoplastic Agents (Paul Calabrese and Bruce A. Chabner).
Graziano, R. F. et al. (1995) J. Immunol. 155 (10): 4996-5002.
Greenbaum et al., Genome Biology (2003) vol. 4, Issue 9, pp. 117.1-117.8.
Greenberg, J. Immunol. (1986) 136(5):1917.
Gruber et al., Genomics (1998) 54:200-14.
Guo et al., How is mRNA expression predictive for protein expression? A correlation study on human circulating monocytes, Acta Biochim Biophhys Sin (2008) 40:426-436.
Gura (Science, 1997, 278:1041-1042).
Haga, et al., G Protein-Coupled Receptors (1999) ISBN: 0849333849.
Hakomori, S., Cancer Research (1996) 56:5309-5318.
Hall, Stephen S.,"IL-12 at the Crossroads",Science (1995) 268:1432-1434.
Harlow et al., Using Antibodies: A Laboratory Manual: Portable Protocol NO (1999) ISBN 0879695447.
Haupt et al., 2002, Exp. Biol. Med. 227:227-237.
Hayat, M.A., Microscopy, Immunohistochemistry and Antigen Retrieval Methods: For Light and Electron Microscopy (2002) ISBN: 0306467704.
Hell et al., Laboratory Investigation (1995) 73:492-496.
Hellstrom et al., "Antibodies for Drug Delivery", in Controlled Drug Delivery (2nd Ed.), 1987.
Herbert et al., The Dictionary of Immunology, Academic Press, 3rd Edition, London (1985) p. 58-59.
Hewitt et al., BMC Cancer, 6:1471-2407 (2006).
Hillier et al., Genome Research (1996) 6:807-828.
Hoetelmans, et al. Applied Immuno. & Molecular Morphology 9 (4) 346-351 (2001).
Holliger, P., et al. (1993) Proc. Natl. Acad. Sci. USA 90: 6444-6448.
Horikawa, Y., et al., Bell GI Nat. Genet. (Oct. 2000) 26(2):163-75.
Hsu, in Tissue Culture Methods and Applications, Kruse and Patterson, Eds (1973) Academic Press, NY, see abstract, p. 764.
Huston et al. (1988) Proc. Natl. Acad. Sci. USA 85: 5879-5883.
Intellectual Property Office of New Zealand, Examination Report re Patent Application No. 595896, dated Oct. 21, 2011 (3 pages).
International Search Report, PCT/EP2005/005410, dated Aug. 30, 2005, 4 pgs.
Int'l Prelim. Report on Patentability for PCT/EP2008/004197, dated Dec. 1, 2009.
Int'l Preliminary Report on Patentability for PCT/EP20131001331 dated Nov. 20, 2014 (7 pages).
Int'l Search Report for PCT/EP2008/004197, dated Nov. 21, 2008.
Int'l Search Report for PCT/EP2012/001991 dated Sep. 13, 2012.
Int'l Search Report for PCT/EP2013/001331 dated Oct. 7, 2013.
J. Golay, M. Introna, Arch. Biochem. Biophys (2012), doi: 10.1016/j.abb 2012.02.011.
Jang et al., Clinical Exp. Metastasis (1997) 15:469-483.
Jiang et al (J. Biol. Chem, 2003, 278(7) 4763-4769).
Jones et al., Replacing the complementarity-determining regions in a human antibody with those from a mouse, Nature 321: 522-525, 1986.
Jung et al., Mol. Cells (2001) 12:41-49.

Kaiser (Science, 2006, 313; 1370).
Karam & Leblond, "Dynamics of Epithelial Cells in the Corpus of the Mouse Stomach", The Anatomical Record 236:259-279 (1993).
Karpovsky et al. (1984) J. Exp. Med. 160: 1686.
Kasinrerk et al., Hybrid Hybridomics (2002) 21:287-293.
Kast et al., Cell (1989) 59:603-614.
Kayyem et al., Eur. J. Biochem. (1992) 208:1-8.
Keogh et al., J. Immunol. (2001) 167:787-96.
Kessels et al., Nat. Immunol. (2001) 2:957-61.
Klamp Thorsten et al: "Highly Specific Auto-Antibodies against Claudin-18 Isoform 2 Induced by a Chimeric HBcAg Virus-Like Particle Vaccine Kill Tumor Cells and Inhibit the Growth of Lung Metastases". Cancer Research. vo 1. 71. No. 2. Jan. 15, 2011 (Jan. 15, 2011). pp. 516-527. XP002678744.
Kohler and Milstein, Nature 256: 495 (1975).
Kohler, "Immunoglobulin chain loss in hybridoma lines," Proc. Natl. Aca. Sco. USA, vol. 77, No. 4, pp. 2197-2199, Apr. 1980.
Koslowski et al., Multiple Splice Variants of Lactate Dehydrogenase C Selectively Expressed in Human Cancer, Cancer Research (2002) 62:6750-6755.
Kozak, 1991, J. Biol. Chem. 266: 19867-19870.
Kraus et al., in Methods in Molecular Biology series, Recombinant antibodies for cancer therapy ISBN-0-89603-918-8 2003.
Kreig et al., Nature (1995) 374:546-9.
Krontiris and Capizzi, Internal Medicine, 4th Edition, Editor-in-chief Jay Stein, Elsevier Science (1994) Chapters 71-72, pp. 699-715.
"Krukenberg tumor", https://en.wikipedia.org/wiki/Krukenberg_tumor, found on Oct. 15, 2015, 2 pages. Not in English.
Kuby, Janis Immunology, W. H. Freeman and Company New York, N Y (1992).
Kurotani , et al., Secretoglobin3A2/uterglobin-related protein 1 is a novel marker for pulmonary carcinoma in mice and humans, Lung Cancer 71, pp. 42-48 (2011).
Landor M. (1995) Maternal-fetal transfer of immunoglobulines, Ann. Allergy Asthma Immunol. 74: 279-283.
Lee et al., Genomics (2000) 70:354-63.
Lemoine et al., Methods Mol. Biol. (1997) 75:441-7.
Lemon, W.J., et al., Identification of candidate lung cancer susceptibility genes in mouse using oligonucleotide arrays, Journal of Medical Genetics (2002) 39:644-655.
Leuenberger, et al. "A multilingual glossary of biotechnological terms: (IUPAC Recommendations)", Helvetica Chimica Acta, CH-4010 Basel, Switzerland, (1995).
Liu, MA et al. (1985) Proc. Natl. Acad. Sci. USA 82: 8648.
Lohi et al., J. Biol. Chem. (2002) 277:14246-54.
Lynch (1998) Identification and Expression of G-Protein Coupled Receptors, Receptor Biochemistry and Methodology, ASIN: 0471183105.
Lynch et al. (1991) Eur. J. immunol. 21:1403-10.
Maloy et al., Proc. Natl. Acad. Sci. USA (2001) 98:3299-303.
Mar. 25, 2004, "Human gene of the invention NOV20a Seq ID No. 489", XP002656866.
Matsushita et al (FEBS Letters, 1999, vol. 443, pp. 348-352).
Matz et al. Nucleic Acids Research, 1999, vol. 27, No. 6, 1558.
Merrifield (1964).
Monteiro, R. C. et al. (1992) J. Immunol. 148: 1764.
Morris, Glenn E., Epitope Mapping Protocols (Methods in Molecular Biology) ISBN-089603-375-9, 1996.
Morrison, "Transfectomas Provide Novel Chimeric Antibodies," Science 229: pp. 1202-1207, (1985).
Morton, H. C. et al. (1996) Critical Reviews in Immunology 16: 423-440.
Nature 321: 522-525, May 29, 1986.
Nature 332: 323-327, Mar. 24, 1988.
Nature 341: 544-546, Oct. 12, 1989.
NCBI , "claudin-18A2.1 [*Homo sapiens*]." Retrieved from the Internet Sep. 15, 2009, http://www.ncbi.nim.nih.gov/protein/16224169.
NCBI , "*Homo sapiens* claudin-18A2.1 mRNA, complete cds, alternatively spliced." Retrieved from the Internet Sep. 15, 2009, http://www.ncbi.nim.nih.gov.nuccore/16224168?report=genbank &log$=seqview.

(56) References Cited

OTHER PUBLICATIONS

Neddleman and Wunsch, 1970, J. Mol. Biol. 48, 443.
Niimi et al., Am. J. Hum. Genet. (2002) 70:718-25.
Niimi, Mol. Cell. Biol. 21:7380-90, 2001.
Non-Final Office Action dated Oct. 19, 2010 in U.S. Appl. No. 12/326,997.
Notice of Allowance dated Jul. 3, 2013 in U.S. Appl. No. 12/423,153.
O'Dowd et al., Discovery of Three Novel G-Protein-Coupled Receptor Genes, Genomics (1998) 47-310-313.
Office Action dated Dec. 11, 2012 in U.S. Appl. No. 12/423,153.
Office Action dated Mar. 22, 2012 in U.S. Appl. No. 12/423,153.
Office Action dated Jul. 19, 2012 in U.S. Appl. No. 12/423,153.
Office Action dated Sep. 9, 2011 in U.S. Appl. No. 12/423,153.
Office Action for U.S. Appl. No. 12/601,488, dated Apr. 19, 2012.
Office Action with English translation for Japanese patent application No. JP2004-554414. 2004.
Okazaki, Y., et al., Analysis of the mouse transcriptome based on functional annotation of 60,770 full-length cDNAs, Nature (2002) 420(6915):563-573.
Orntoft et al., Genome-wide Study of Gene Copy Numbers, Transcripts, and Protein Levels in Pairs of Non-invasive and Invasive Human Transitional Cell Carcinomas, Molecular & Cellular Proteomics (2002) 1:37-45.
Ossendorp et al., Immunol. Lett. (2000) 74:75-9.
Ossendorp et al., J. Exp. Med. (1998) 187:693-702.
Ozturk, et al., "Loss of Antibody Productivity During Long-Term Cultivation of a Hybridoma Cell Line in Low Serum and Serum-Free Media," Hybridoma, Apr. 2009, 9(2): 167-175.
Pardoll, D., Nature Medicine Vaccine Supplement (1998) 4:525-531.
Park et al., Cancer Epidemiol Biomarkers Prev. (2002) 11:739-44.
Paulus (Behring Ins. Mitt. (1985) No. 78, 118-132.
PCT Int'l Bureau, IPRP for Appln No. PCT/EP2006/011302. 2006.
PCT Int'l Bureau, ISR for Appln No. PCT/EP2006/011302. 2006.
PCT Int'l Bureau, Written Opinion of the Int'l Searching Authority for Appln No. PCT/EP2006/011302. 2006.
Pearlman et al. Dig. Dis. Sci (2000) 45:298-05.
Pearson and Lipman, 1988, Proc. Natl Acad. Sci. USA 85, 2444.
Pennisi, Science (1997) 276:1023-1024.
Pinchera et al. (eds) pp. 475-506 (1985) Analysis Results, and Future Prospective of the Therapeutic Use of Radiolabeled Antibodi in Cancer Therapy, in Monoclonal Antibodies for Cancer Detection and Therapy.
Poljak, R. J. , et al. (1994) Structure 2: 1121-1123.
Pollock, et al. (1999) J. Immunol. Meth. 231: 147-157.
Queen, C. et al. (1989) Proc. Natl. Acad. Sci. U. S. A. 86: 10029-10033.
Rader, et al. J. Bio. Chem. (May 2000) 275 (18):13668-76.
Ragupathi et al., 2005, J. Immunol. 174:5706-5712.
Ranade, V.V. (1989) J. Clin. Pharmacol. 29: 685.
Reisfeld et al. (eds.) pp. 243-256 (Alan R. Liss, Inc. 1985).
Reiter et al., Peptide-specific killing of antigen-presenting cells by a recombinant antibody-toxin fusion protein targeted to Major Histocompatibility Complex/Peptide Class I Complexes with T Cell Receptor-like Specificity, Proc. Natl. Acad. Sci. USA (1997) 94:4631-4636.
Remington: The Science and Practice of Pharmacy, 19th Edition, Gennaro, Ed., Mack Publishing CO., Easton, PA, 1995.
Restriction Requirement dated Mar. 24, 2011 in U.S. Appl. No. 12/423,153.
Riddel, et al., Science (1992) 257:238.
Ridge et al., Nature (1998) 393:474.
Riechmann et al., "Reshaping human antibodies for therapy,", Nature, vol. 332, 24, pp. 323-327, (1998).
Riemer A B et al: "Matching of trastuzumab (Herceptin (R)) epitope mimics onto the surface of Her-2/neu—a new method of epitope definition", Molecular Immunology, Pergamon, GB Bd. 42, Nr. 9, 1. Mai 2015 (May 1, 2005), Seiten 1121-1124.
Robinson et al. (eds.), pp. 623-653 (Marcel Dekker, Inc. 1987).
Robinson Handbook of Flow Cytometry Methods. Wiley-Liss, New York, 1993.
Roguska et al. 2004, Curr. Prot. Pharmaol., Unit 9.7 (Abstract).
Roitt, I., Essential Immunology (1991) 7th Ed., Blackwell Scientific Publications, Oxford.
Rossi et al., Am. J. Clin. Pathol. 124: 295 (2005).
Rudikoff et al (PNAS, USA, 1982,79: 1979-1983).
Rudolph, M. & Wilson, I.A., The specificity of TCR/pMHC interaction, Current Opinion in Immunology (2002) 14:52-65.
Sahin Ugur et al: "Claudin-18 splice variant 2 is a pan-cancer target suitable for therapeutic antibody development". Clinical Cancer Research. The American Association for Cancer Research. US. vo 1. 14. No. 23. Dec. 1, 2008 (Dec. 1, 2008). pp. 7624-7634. XP002588324.
Sambrook et al., Molecular Cloning: A Laboratory Manual, 2nd Edition (1989) Cold Spring Harbor Laboratory Press, Cold Spring Harbor, N.Y.
Sanada et al., 2006, Journal of Pathology, vol. 208, 633-642.
Scallon et al., 2006, J. Immunother. 29:351-364.
Scheurle et al., Cancer Gene Discovery Using Digital Differential Display, Cancer Res., 60:4037-4043 (2000).
Schmitt et al., Nucleic Acids Research (1999) 27:4251-4260.
Schonberger et al., Nature (1998) 393:480.
Schroff, Robert W., et al., T65 Antigen Modulation in a Phase I Monoclonal Antibody Trial with Chronic164 Lymphocytic Leukemia Patients, The Journal of Immunology, vol. 133, No. 3, 1641-1648, Sep. 1984.
Science 229: 1202-1207, Sep. 20, 1985.
Science 242: 423-426, Oct. 21, 1988.
Secretoglobin Family 3A member 2 Precursor—*Homo sapiens* (Human), http//www.uniprot.org/uniprot/Q96P, dated Nov. 1, 2012 (4 pages).
Sep. 29, 2000, "*Homo sapiens* cDNA: FLJ21458 fis, clone COL04713", XP002656867.
Shankavaram et al., Transcript and protein expression profiles of the NCI-60 cancer cell panel: an integromic microarray study, Mol. Cancer Ther. (2007) 6(3):820-32.
Shepherd et al., Monoclonal Antibodies: A Practical Approach (2000) ISBN 0-19-63722-9.
Shi et al., J. Histochem. Cytochem. (1991) 39:741-748.
Shields et al. (2002) JBC, 277: 26733.
Shin et al., Lab.Invest. (1991) 64:693-702.
Shinakawa T et al, The Journal of Biological Chemistry, Jan. 31, 2003, vol. 278, No. 5, p. 3466-3473.
Shin-iciro Kitajiri et al., Expression patterns of claudins, tight junction adhesion molecules, in the inner ear, Hearing Research, vol. 187, Jan. 31, 2004, pp. 25-34.
Shiomi et al. (Tumori, 2001, 87(3): Abstract).
"Siegelringkarzinom", https://de.wikipedia.org/wiki/Siegelringkarzinom, found on Oct. 15, 2015, 2 pages. Not in English.
Smith and Waterman, 1981, Ads App. Math. 2, 482.
So et al, Mol. Cells (1997) 7:178-186.
Spieker-Polet et al., Proc. Natl. Acad. Sci. U.S.A. 92:9348 (1995).
Spiller et al., J. Immunol. Methods (1999) 224:51-60.
Spiro, Robert G., Protein Glycosylation: nature, distribution, enzymatic formation, and disease implications of glycopeptide bonds, Glycobioloby vol. 12, No. 4, pp. 43R-56R (2002).
Stanislawski et al, Nat Immunol. (2001) 2:962-70.
Stockwin and Holmes, 2003, Biochem. Soc. Trans. 31:433-436.
Strejan et al. (1984) J. Neuroimmunol. 7: 27.
Taber's Cyclopedic Medical Dictionary (1985) F.A. Davis Company, Philadelphia, p. 274.
Tachihara-Yoshikawa et al., Expression of Secretoglobin3A2 (SCGB3A2) in Primary Pulmonary Carcinomas, Fukushima J. Med. Sci., vol. 54, No. 2 (2008).
Tatsuya Haga, "G Protein-Coupled Receptors" ISBN: 0849333849 (2005).
Teeling et al., 2006, J. Immunol. 177:362-371.
Terminal Disclaimer filed Mar. 7, 2013 in U.S. Appl. No. 12/423,153.
Terminal Disclaimer filed Jun. 17, 2013 in U.S. Appl. No. 12/423,153.

(56) References Cited

OTHER PUBLICATIONS

Thorpe et al., "The Preparation and Cytotoxic Properties of Antibody-Toxin Conjugates" Immunol. Rev., 62: 119-58 (1982).
Thorpe, Antibody Carriers of Cytotoxic Agents in Cancer Therapy: A Review, in Monoclonal Antibodies '84: Biological and Clinical Applications, 1985.
Tian et al, Integrated Genomic and Proteomic Analyses of Gene Expression in Mammalian Cells, Molecular & Cellular Proteomics (2004) 3:960-969.
Tremblay et al., Mol. Cell Biochem, (2002) 230-31.
Umezawa et al., (1988) Biochem. Biophys. Res. Commun. 153: 1038.
Vallejo et al., Biochimie (2000) 82:1129-1133.
Van Der Bruggen et al., Science (1991) 254:1643-1647.
Vang et al. 2004 (abstract).
Vasmatzis et al., Proc. Natl. Acad. Sci. USA (1998) 95:300-304.
Velders MP et al., British Journal of Cancer (1998), 78(4), 478-483.
Verma, R., et al. (1998) J. Immunol. Meth. 216: 165-181.
Ward et al., "Binding activities of a repertoire of single immunoglobulin variable domains secreted from *Escherichia coli*," Nature 341: 544-546, 1989.
Weiner L. M. et al, 2009, Lancet 373: 1033-1040.
Weiner, L. M., 1999, Seminars in Oncology 26: 41-50.
Welschof and Kraus, Recombinant antibodies for cancer therapy ISBN-0-89603-918-8, 2003.
Wentworth et al., Mol. Immunol. (1995) 32:603-12.
Westwood, Olwyn et al. "Epitope Mapping: A Practical Approach" Practical Approach Series, 248, 2001.
Wheeler et al., Nucleic Acids Research (2000) 28:10-14.
Yu Guan-zhen et al., 2007.
Zellner et al., Clin. Can. Res. (1998) 4:1797-1802.
Zheng, P. et al., Proc. Natl. Acad. Sci. USA (1998) 95(11):6284-6289.
Zimmer, Cell Motility and the Cyloskeleton (1991) 20:325-337.

U.S. Appl. No. 10/537,002, US 2006/0035852 A1, U.S. Pat. No. 7,757,933.
U.S. Appl. No. 12/326,997, US 2009/0155817 A1, U.S. Pat. No. 8,088,588.
U.S. Appl. No. 12/423,153, US 2009/0208498 A1, U.S. Pat. No. 8,586,047.
U.S. Appl. No. 13/296,620, US 2012/0258091 A1, U.S. Pat. No. 8,637,012.
U.S. Appl. No. 14/043,109, US 2014/0186338 A1.
U.S. Appl. No. 14/821,411, US 2015/0337052 A1.
U.S. Appl. No. 11/596,649, US 2008/0166350 A1, U.S. Pat. No. 9,044,382.
U.S. Appl. No. 14/676,254, US 2015/0315287 A1.
U.S. Appl. No. 12/094,530, US 2009/0169547 A1, U.S. Pat. No. 8,168,427.
U.S. Appl. No. 13/306,545, US 2012/0164160 A1, U.S. Pat. No. 9,499,609.
U.S. Appl. No. 13/425,538, US 2012/0195830 A1, U.S. Pat. No. 9,212,228.
U.S. Appl. No. 14/661,882, US 2015/0252104 A1.
U.S. Appl. No. 14/661,846, US 2015/0252103 A1.
U.S. Appl. No. 15/069,511, US 2016/0185860 A1.
U.S. Appl. No. 12/601,488, US 2010/0166779 A1, U.S. Pat. No. 8,425,902.
U.S. Appl. No. 14/397,244, US 2015/0147763 A1, U.S. Pat. No. 9,512,232.
U.S. Appl. No. 14/401,899, US 2015/0132253 A1.
U.S. Appl. No. 14/401,557, US 2015/0157711 A1, U.S. Pat. No. 9,433,675.
U.S. Appl. No. 15/231,185, US 2016/0339101 A1.
U.S. Appl. No. 14/442,445, US 2016/0272711 A1.
U.S. Appl. No. 14/769,046, US 2015/0374789 A1.
U.S. Appl. No. 14/777,231, US 2016/0008465 A1.
U.S. Appl. No. 15/448,831, US 2017/0215536 A1.

* cited by examiner

Figure 1

|          | 1   |           | TMhelix    |            |            |            |            | 50 |
|----------|-----|-----------|------------|------------|------------|------------|------------|----|
| HsCld18.1 |    | NSTTCQSVVA | FLLSILGLAG | CIAATCMDMW | STQDLYDNPV | TSVFQYEGLW |            |    |
| HsCld18.2 |    | MAVTACQSLG | FVVSLIGLAG | IIAATCMDQW | STQDLYNNPV | TAVFNYQGLW |            |    |
| MmCld18.2 |    | MSVTACQGLG | FVVSLIGFAG | IIAATCMDQW | STQDLYNNPV | TAVFNYQGLW |            |    |
| Consensus |    | MsvTaCqglg | Fvvslig.ag | iIAATCmDqw | STQDLYnNPV | TaVFnYqGLW |            |    |

|          | 51  |           |            |            | TMhelix    |            | 100 |
|----------|-----|-----------|------------|------------|------------|------------|-----|
| HsCld18.1 |    | RSCVRQSSGF | TECRPYFTIL | GLPAMLQAVR | ALMIVGIVLG | AIGLLVSIFA |     |
| HsCld18.2 |    | RSCVRESSGF | TECRGYFTLL | GLPAMLQAVR | ALMIVGIVLG | AIGLLVSIFA |     |
| MmCld18.2 |    | RSCVRESSGF | TECRGYFTLL | GLPAMLQAVR | ALMIVGIVLG | VIGLLVSIFA |     |
| Consensus |    | RSCVResSGF | TECRgYfTlL | GLPAMLQAVR | ALMIVGIVLG | aIGLLVSIFA |     |

|          | 101 |           |            |            |            | TMhelix    | 150 |
|----------|-----|-----------|------------|------------|------------|------------|-----|
| HsCld18.1 |    | LKCIRIGSME | DSAKANMTLT | SGIMFIVSGL | CAIAGVSVFA | NMLVTNFWMS |     |
| HsCld18.2 |    | LKCIRIGSME | DSAKANMTLT | SGIMFIVSGL | CAIAGVSVFA | NMLVTNFWMS |     |
| MmCld18.2 |    | LKCIRIGSMD | DSAKAKMTLT | SGLFFIISGI | CAIIGVSVFA | NMLVTNFWMS |     |
| Consensus |    | LKCIRIGsMe | DSAKAnMTLT | SGimFivSGl | CAiaGVSVFA | NMLVTNFWMS |     |

|          | 151 |           |            |            |            | TMhelix    | 200 |
|----------|-----|-----------|------------|------------|------------|------------|-----|
| HsCld18.1 |    | TAHMYTGMGG | M---VQTVQT | RYTFGAALFV | GWVAGGLTLI | GGVMMCIACR |     |
| HsCld18.2 |    | TAHNYTWAGG | M---VQTVQI | RYTFGAALFV | GWVAGGLTLI | GGVMMCIACR |     |
| MmCld18.2 |    | TAHNYSGMGG | MGGMVQTVQT | RYTFGAALFV | GWVAGGLTLI | GGVMMCIACR |     |
| Consensus |    | TAHnYtGaGG | M...VQTVQt | RYTFGAALFV | GWVAGGLTLI | GGVmmCIACR |     |

|          | 201 |           |            |            |            |            | 250 |
|----------|-----|-----------|------------|------------|------------|------------|-----|
| HsCld18.1 |    | GLAPEETNYK | AVSYHASGHS | VAYKPGGFKA | STGFGSNTKN | KKIYDGGART |     |
| HsCld18.2 |    | GLAPEETNYK | AVSYHASGHS | VAYKPGGFKA | STGFGSNTKN | KKIYDGGART |     |
| MmCld18.2 |    | GLTPDDSNFK | AVSYHASGQN | VAYRPGGFKA | STGFGSNTRN | KKIYDGGART |     |
| Consensus |    | GLaPeetNyK | AVSYHASGhs | VAYkPGGFKA | STGFGSNTkN | KKIYDGGART |     |

|          | 251 |           | 264  |             |
|----------|-----|-----------|------|-------------|
| HsCld18.1 |    | EDEVQSYPSK | HDYV | (SEQ ID NO: 1) |
| HsCld18.2 |    | EDEVQSYPSK | HDYV | (SEQ ID NO: 2) |
| MmCld18.2 |    | EDDEQSHFTA | YDYV | (SEQ ID NO: 3) |
| Consensus |    | EDevQSYPsK | hDYV | (SEQ ID NO: 4) |

Heavy chain

```
                  1         Leader
H-43-14A_2    MAWVWTLLFL MAAAQSIQAQ IQLVQSGPEL KKPGETVKIS CKASGYTFTD  CDR1
H-35-22A_1    MNFGLSLIFL VLVLKGVQCE VLVESGGGL VKPGGSLKLS CAASGFTFSS 51                                                100
H-43-14A_2    YSIHWVKQAP GKGLKWMGWI NTETGEPTYA DDFKGRFAFS LETSASTAYL    CDR2
H-35-22A_1    YAMSWVRQTP EKRLEWVATI SDGGSYSYYP DNVKGRFTIS RDNAKNNLYL 101                              140
H-43-14A_2    QINNLKNEDT ATYFCARRTG FD------YW GQGTTLTVSS   (SEQ ID NO: 7)     CDR3
H-35-22A_1    QMSRLKSEDT AIYYCARDSY YDNSIVRDW GQGTTLTVSS    (SEQ ID NO: 15)
```

Light chain

```
                  1         Leader
LN-43-14A_    MRFSAQLLGL LVLWIPGSTA DIVMTQAAFS IPVTLGTSAS ISCRSSKNLL    CDR1
LN-35-22A_    MRTPAQFLGI LLLWFPGSRC DIKMTQSPSS MYASLGERVS ITCKASQDIN 51                                                100
LN-43-14A_    HSDGITYLYW YLQRPGQSPQ LLIYRVSNLA SGVPNRFSGS GSGTDFTLRI   CDR2
LN-35-22A_    -----TFLSW FQQKPGKSFK TLIYRTNRLI DGVPSRFSGS GSGQDYSLTI 101                       132
LN-43-14A_    SRVEAEDVGV YYCVQVLELP FTCGGTKLE IK    (SEQ ID NO: 11)    CDR3
LN-35-22A_    SSLDYEDMGI YYCLQYDEFP LHCGAGTKLE LK    (SEQ ID NO: 19)
```

ANTIBODIES AGAINST CLAUDIN 18.2 USEFUL IN CANCER DIAGNOSIS

RELATED APPLICATIONS

This application is a divisional of U.S. application Ser. No. 14/397,244, which is a U.S. National Stage Application submitted under 35 U.S.C. 371 of International Application Serial Number PCT/EP2013/001331, filed on May 6, 2013, which claims priority to International Application Serial Number PCT/EP2012/001991, filed on May 9, 2012. The entire teachings of the above-referenced Applications are incorporated herein by reference.

BACKGROUND

Claudins are integral membrane proteins located within the tight junctions of epithelia and endothelia. Claudins are predicted to have four transmembrane segments with two extracellular loops, and N- and C-termini located in the cytoplasm. The claudin (CLDN) family of transmembrane proteins plays a critical role in the maintenance of epithelial and endothelial tight junctions and might also play a role in the maintenance of the cytoskeleton and in cell signaling.

The claudin 18 (CLDN18) molecule is an integral transmembrane protein (tetraspanin) having four membrane spanning hydrophobic regions and two extracellular loops (loop1 embraced by hydrophobic region 1 and hydrophobic region 2; loop2 embraced by hydrophobic regions 3 and 4). CLDN18 exists in two different splice variants, which are described in mouse and in human (Niimi, Mol. Cell. Biol. 21:7380-90, 2001). The splice variants (Genbank accession number: splice variant 1 (CLDN18.1): NP_057453, NM_016369, and splice variant 2 (CLDN18.2): NM_001002026, NP_001002026) have a molecular weight of approximately 27.9/27.72 kD. The splice variants CLDN18.1 and CLDN18.2 differ in the N-terminal portion which comprises the first transmembrane (TM) region and loop1, whereas the primary protein sequence of the C-terminus is identical; see FIG. 1.

CLDN18.1 is selectively expressed on cells of normal lung, whereas CLDN18.2 is expressed only on gastric cells. However, CLDN18.2 expression in normal stomach is restricted to the differentiated short-lived cells of stomach epithelium. CLDN18.2 expression has been identified in various tumor tissues. For example, CLDN18.2 has been found to be expressed in pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis.

The differential expression of CLDN18.2 between cancer and normal cells, its membrane localization, its absence from the vast majority of toxicity relevant normal tissues, its restriction of expression to a dispensable cell population in stomach, differentiated gastric cells, which can be replenished by target-negative stem cells of the stomach, makes CLDN18.2 an attractive target for cancer immunotherapy and the use of antibody-based therapeutics for targeting CLDN18.2 in cancer therapy promises a high level of therapeutic specificity.

The clinical application of CLDN18.2-targeting antibodies faces the obstacle that human CLDN18.2 is highly homologous to human CLDN18.1. CLDN18.2-specific antibodies targeting the N-terminal extracellular domain of CLDN18.2 displaying sequence differences between human CLDN18.2 and human CLDN18.1 could successfully be established. Attempts to produce antibodies targeting the N-terminal portion of CLDN18.2 and having properties making them clinically applicable for diagnostic purposes, e.g. for detection of CLDN18.2 expression in cells of cancer tissue sections, failed.

Surprisingly, the present inventors found that antibodies directed against a certain epitope located within the C-terminal portion of CLDN18.2 fulfill the criteria for the diagnostic applicability of antibodies, in particular for detecting and identifying cells expressing CLDN18.2. Most surprisingly, these antibodies although directed against a sequence which is identical between CLDN18.1 and CLDN18.2 do not target non-cancerous lung cells.

The antibodies of the invention are useful, for example, in diagnosing cancer and/or in determining whether cancer cells express CLDN18.2. Preferably, a cancer disease or a cancer cell is characterized by surface expression of CLDN18.2. Cancer cells expressing CLDN18.2 are suitable targets for therapies targeting CLDN18.2 such as therapy with antibodies directed against CLDN18.2. In one embodiment, cancer cells express or aberrantly express CLDN18.2 while the corresponding normal cells do not express CLDN18.2 or express CLDN18.2 at a lower level. The cells expressing CLDN18.2 are preferably selected from the group consisting of tumorigenic gastric, esophageal, pancreatic, lung, ovarian, colon, hepatic, head-neck, and gallbladder cancer cells.

SUMMARY OF THE INVENTION

The present invention relates to an antibody or antigen-binding fragment thereof which
(i) binds to a peptide having the amino acid sequence TEDEVQSYPSKHDYV (SEQ ID NO: 5) or EVQSYPSKHDYV (SEQ ID NO: 6) and/or
(ii) binds to claudin 18.2 (CLDN18.2), wherein said antibody or antigen-binding fragment thereof binds to CLDN18.2 by binding at least to an epitope within CLDN18.2 having the amino acid sequence TEDEVQSYPSKHDYV (SEQ ID NO: 5) or EVQSYPSKHDYV (SEQ ID NO: 6).

In one embodiment, said CLDN18.2 is cell surface membrane-bound CLDN18.2. In one embodiment, said CLDN18.2 is present on cancer cells, wherein said cancer cells are preferably CLDN18.2 expressing cancer cells. In one embodiment, said cancer cells are selected from the group consisting of gastric, esophageal, pancreatic, lung, ovarian, colon, hepatic, head-neck, and gallbladder cancer cells. In one embodiment, an antibody or antigen-binding fragment of the invention does not bind to non-cancerous cells except stomach epithelial cells. In one embodiment, an antibody or antigen-binding fragment of the invention does not bind to non-cancerous lung cells. In one embodiment, an antibody of the invention is a chimeric, human or humanized antibody. In one embodiment, an antibody of the invention is a monoclonal antibody.

In these and further aspects the present invention relates to an antibody comprising:
(I) an antibody heavy chain comprising:
(i) an antibody heavy chain sequence according to SEQ ID NO: 7 or a variant thereof, (ii) at least one, preferably two, more preferably all three of the CDR sequences of an antibody heavy chain sequence according to SEQ ID NO: 7 or a variant thereof, or (iii) a CDR3 sequence according to SEQ ID NO: 10 or a variant thereof and preferably further comprising a CDR1 sequence according to SEQ ID NO: 8 or a variant thereof and/or a CDR2 sequence according to SEQ ID NO: 9 or a variant thereof, and/or (II) an antibody light chain comprising:

(i) an antibody light chain sequence according to SEQ ID NO: 11 or a variant thereof, (ii) at least one, preferably two, more preferably all three of the CDR sequences of an antibody light chain sequence according to SEQ ID NO: 11 or a variant thereof, or (iii) a CDR3 sequence according to SEQ ID NO: 14 or a variant thereof and preferably further comprising a CDR1 sequence according to SEQ ID NO: 12 or a variant thereof and/or a CDR2 sequence according to SEQ ID NO: 13 or a variant thereof.

In the above and further aspects the present invention also relates to an antibody comprising:

(I) an antibody heavy chain comprising:

(i) an antibody heavy chain sequence according to SEQ ID NO: 15 or a variant thereof, (ii) at least one, preferably two, more preferably all three of the CDR sequences of an antibody heavy chain sequence according to SEQ ID NO: 15 or a variant thereof, or (iii) a CDR3 sequence according to SEQ ID NO: 18 or a variant thereof and preferably further comprising a CDR1 sequence according to SEQ ID NO: 16 or a variant thereof and/or a CDR2 sequence according to SEQ ID NO: 17 or a variant thereof, and/or (II) an antibody light chain comprising:

(i) an antibody light chain sequence according to SEQ ID NO: 19 or a variant thereof, (ii) at least one, preferably two, more preferably all three of the CDR sequences of an antibody light chain sequence according to SEQ ID NO: 19 or a variant thereof, or (iii) a CDR3 sequence according to SEQ ID NO: 22 or a variant thereof and preferably further comprising a CDR1 sequence according to SEQ ID NO: 20 or a variant thereof and/or a CDR2 sequence according to SEQ ID NO: 21 or a variant thereof.

In preferred embodiments, an antibody of the invention comprises an antibody heavy chain comprising a gamma-1 heavy chain constant region, preferably a human gamma-1 heavy chain constant region and/or comprises an antibody light chain comprising a kappa light chain constant region.

In the above and further aspects the present invention relates to an antibody produced by or obtainable from a hybridoma cell deposited at the DSMZ (Inhoffenstr. 7B, 38124 Braunschweig, Germany) and having one of the following designations and accession numbers:

1. muAB 43-14A, accesssion no. DSM ACC3144, deposited on Oct. 6, 2011; or 2. muAB 35-22A, accesssion no. DSM ACC3143, deposited on Oct. 6, 2011.

Antibodies of the invention are designated herein by referring to the designation of the antibody and/or by referring to the clone producing the antibody, e.g. muAB 43-14A.

Further preferred antibodies are those having the specificity of the antibodies produced by and obtainable from the above-described hybridomas and, in particular, those comprising an antigen binding portion or antigen binding site, in particular a variable region, identical or highly homologous to that of the antibodies produced by and obtainable from the above-described hybridomas. It is contemplated that preferred antibodies are those having CDR regions either identical or highly homologous to the CDR regions of antibodies produced by and obtainable from the above-described hybridomas. By "highly homologous" it is contemplated that from 1 to 5, preferably from 1 to 4, such as 1 to 3 or 1 or 2 substitutions may be made in each CDR region. Particularly preferred antibodies are the chimerized and humanized forms of the antibodies produced by and obtainable from the above-described hybridomas.

Thus, an antibody of the invention may be selected from the group consisting of (i) an antibody produced by or obtainable from a clone deposited under the accession no. DSM ACC3144 (muAB 43-14A) or DSM ACC3143 (muAB 35-22A), (ii) an antibody which is a chimerized or humanized form of the antibody under (i), (iii) an antibody which has the specificity of the antibody under (i), and (iv) an antibody comprising the antigen binding portion or antigen binding site of the antibody under (i). The antigen binding portion or antigen binding site of the antibody under (i) may comprise the variable region of the antibody under (i). Furthermore encompassed by the present invention are antigen-binding fragments of the antibodies described herein.

An antibody of the invention is preferably able to bind to CLDN18.2 in its native, i.e. naturally occurring or non-denatured state, or in its denatured state.

In one embodiment, an antibody of the invention is obtainable by a method comprising the step of immunizing an animal with a peptide comprising, preferably consisting of the amino acid sequence of SEQ ID NO: 5 or SEQ ID NO: 6, or an immunologically equivalent peptide, or a nucleic acid or host cell expressing said peptide. Preferably said peptide comprises not more than 110, 100, 90, 80, 70, 60, 50, 40, 30, or 20 contiguous amino acids of CLDN18.2.

In one embodiment, an antibody of the invention is obtainable by a method comprising the step of immunizing an animal with a peptide comprising, preferably consisting of the amino acid sequence of SEQ ID NO: 24 or SEQ ID NO: 25, or an immunologically equivalent peptide, or a nucleic acid or host cell expressing said peptide. Preferably said peptide comprises not more than 110, 100, 90, 80, or 75 contiguous amino acids of CLDN18.2.

Antibodies or antigen-binding fragments of the invention may be coupled, i.e. covalently or non-covalently linked, to other moieties such as detectable labels.

The present invention also relates to a cell such as a hybridoma cell producing an antibody as described herein.

Preferred hybridoma cells are those deposited at the DSMZ (Inhoffenstr. 7B, 38124 Braunschweig, Germany) and having one of the following designations and accession numbers:

1. muAB 43-14A, accesssion no. DSM ACC3144, deposited on Oct. 6, 2011; or 2. muAB 35-22A, accesssion no. DSM ACC3143, deposited on Oct. 6, 2011.

The present invention also relates to a peptide comprising, preferably consisting of the amino acid sequence of SEQ ID NO: 5 or SEQ ID NO: 6, or an immunologically equivalent peptide. Preferably said peptide comprises not more than 110, 100, 90, 80, 70, 60, 50, 40, 30, or 20 contiguous amino acids of CLDN18.2.

The present invention also relates to a peptide comprising, preferably consisting of the amino acid sequence of SEQ ID NO: 24 or SEQ ID NO: 25, or an immunologically equivalent peptide, or a nucleic acid or host cell expressing said peptide. Preferably said peptide comprises not more than 110, 100, 90, 80, or 75 contiguous amino acids of CLDN18.2.

The present invention also relates to nucleic acids comprising genes or nucleic acid sequences encoding antibodies or parts thereof, e.g. an antibody chain, or antigen-binding fragments, or peptides as described herein. Preferably, the nucleic acid of the invention is operatively attached to expression control elements allowing expression in eukaryotic or prokaryotic cells. Control elements ensuring expression in eukaryotic or prokaryotic cells are well known to those skilled in the art.

The nucleic acids of the invention may be comprised in a vector, e.g., a plasmid, cosmid, virus, bacteriophage or another vector used e.g. conventionally in genetic engineering. The vector may comprise further genes such as marker genes which allow for the selection of the vector in a suitable host cell and under suitable conditions. Furthermore, the vector may comprise expression control elements allowing proper expression of the coding regions in suitable hosts. Such control elements are known to the artisan and may include a promoter, a splice cassette, and a translation initiation codon.

Methods for construction of nucleic acid molecules, for construction of vectors comprising nucleic acid molecules, for introduction of vectors into appropriately chosen host cells, or for causing or achieving expression of nucleic acid molecules are well-known in the art.

A further aspect of the present invention relates to a host cell comprising a nucleic acid or vector as disclosed herein.

A further aspect the present invention relates to the detection of CLDN18.2 or CLDN18.2-expressing cells or determination of the quantity of CLDN18.2 or CLDN18.2-expressing cells using an antibody or antigen-binding fragment of the invention. CLDN18.2 or CLDN18.2-expressing cells are detected or the quantity of CLDN18.2 or CLDN18.2-expressing cells is determined by detecting or determining the amount of a complex between CLDN18.2 and an antibody or antigen-binding fragment of the invention.

Formation of a complex indicates the presence of CLDN18.2 or CLDN18.2-expressing cells. Such detection or determination of the amount may be carried out in a number of ways, including but not limited to immunodetection using an antibody or antigen-binding fragment of the invention. Methods for using antibodies to detect peptides or proteins are well known and include ELISA, competitive binding assays, and the like. In general, such assays use an antibody or antibody fragment that specifically binds the target peptide or protein directly or indirectly bound to a label that provides for detection, e.g. indicator enzymes, radiolabels, fluorophores, or paramagnetic particles. The methods of the invention allow quantitative and/or qualitative evaluations, e.g., absolute and/or relative evaluations, of CLDN18.2 levels or of levels of CLDN18.2-expressing cells.

In one aspect, the present invention relates to a method for detecting CLDN18.2 or determining the quantity of CLDN18.2 in a sample comprising the steps of:

(i) contacting a sample with an antibody or antigen-binding fragment of the invention or a conjugate of the invention and (ii) detecting the formation of a complex or determining the quantity of a complex between the antibody, the antigen-binding fragment or the conjugate and CLDN18.2.

In one embodiment, the sample is a cellular sample, i.e. a sample comprising cells such as cancer cells. In this embodiment, the complex is preferably formed between the antibody, the antigen-binding fragment or the conjugate and CLDN18.2 expressed by cells in said sample.

In one aspect, the present invention relates to a method for determining whether cells express CLDN18.2 comprising the steps of:

(i) contacting a cellular sample with an antibody or antigen-binding fragment of the invention or a conjugate of the invention and (ii) detecting the formation of a complex between the antibody, the antigen-binding fragment or the conjugate and CLDN18.2 expressed by cells in said sample.

In one embodiment, the cells in the sample are cancer cells. The complex is preferably formed between the antibody, the antigen-binding fragment or the conjugate and CLDN18.2 expressed by cells in said sample.

Further aspects of the present invention relate to methods of diagnosing or classifying diseases by targeting CLDN18.2 using an antibody or antigen-binding fragment of the invention. These methods provide for the selective detection of cells that express CLDN18.2 thereby differentiating these cells from normal cells not expressing CLDN18.2 or diseased cells not expressing CLDN18.2. Diseases characterized by diseased cells expressing CLDN18.2 are treatable by a therapy targeting CLDN18.2 such as therapy with therapeutic antibodies directed against CLDN18.2. Preferred diseases for a therapy or diagnosis are those in which CLDN18.2 is expressed or aberrantly expressed, in particular cancer diseases, such as those described herein.

In one aspect the present invention relates to methods for diagnosis, detection or monitoring, i.e. determining the regression, progression, course and/or onset, of a cancer disease comprising the detection of CLDN18.2 or CLDN18.2-expressing cells and/or determination of the quantity of CLDN18.2 or CLDN18.2-expressing cells in a biological sample isolated from a patient using an antibody or antigen-binding fragment of the invention. Such methods may be used to detect whether a subject has a cancer disease or is at (increased) risk of developing a cancer disease or, for instance, whether a treatment regimen is efficient.

Thus, in one aspect, the present invention relates to a method for diagnosis, detection or monitoring of cancer comprising the steps of:

(i) contacting a biological sample with an antibody or antigen-binding fragment of the invention or a conjugate of the invention and (ii) detecting the formation of a complex and/or determining the quantity of a complex between the antibody, the antigen-binding fragment or the conjugate and CLDN18.2.

In one embodiment, the biological sample is a cellular sample, i.e. a sample comprising cells such as cancer cells. In this embodiment, the complex is preferably formed between the antibody, the antigen-binding fragment or the conjugate and CLDN18.2 expressed by cells in said sample.

The methods of monitoring according to the invention preferably comprise a detection of and/or determination of the quantity of CLDN18.2 or CLDN18.2-expressing cells in a first sample at a first point in time and in a further sample at a second point in time, wherein the regression, progression, course and/or onset of a tumor disease may be determined by comparing the two samples.

Typically, the level of CLDN18.2 or level of CLDN18.2-expressing cells in a biological sample is compared to a reference level, wherein a deviation from said reference level is indicative of the presence and/or stage of a cancer disease in a subject. The reference level may be a level as determined in a control sample (e.g., from a healthy tissue or subject, in particular a patient without a cancer disease) or a median level from healthy subjects. A "deviation" from said reference level designates any significant change, such as an increase by at least 10%, 20%, or 30%, preferably by at least 40% or 50%, or even more.

Preferably, the presence of CLDN18.2 or CLDN18.2-expressing cells and/or a quantity of CLDN18.2 or CLDN18.2-expressing cells which is increased compared to a reference level, e.g. compared to a patient without a cancer disease, indicates the presence of or risk for (i.e. a potential for a development of) a cancer disease in the patient.

A quantity of CLDN18.2 or CLDN18.2-expressing cells which is decreased compared to a biological sample taken earlier from a patient may indicate a regression, a positive course, e.g. a successful treatment, or a reduced risk for an onset of a cancer disease in a patient.

A quantity of CLDN18.2 or CLDN18.2-expressing cells which is increased compared to a biological sample taken earlier from a patient may indicate a progression, a negative course, e.g. an unsuccessful treatment, recurrence or metastatic behaviour, an onset or a risk for an onset of a cancer disease in said patient.

In one aspect, the present invention relates to a method for determining whether a cancer is treatable by a cancer therapy targeting CLDN18.2 comprising the steps of:

(i) contacting a sample comprising cancer cells with an antibody or antigen-binding fragment of the invention or a conjugate of the invention and (ii) detecting the formation of a complex between the antibody, the antigen-binding fragment or the conjugate and CLDN18.2.

The complex is preferably formed between the antibody, the antigen-binding fragment or the conjugate and CLDN18.2 expressed by cancer cells in said sample.

Such methods may be used to detect whether a patient is suitable for a therapy involving the targeting of cells expressing CLDN18.2 such as a therapy using antibodies exerting one or more immune effector functions such as cytotoxic CLDN18.2 specific antibodies, e.g. antibodies labeled with a cytotoxic substance such as a toxin or a radiolabel or inducing a cell killing mechanism such as CDC or ADCC. Diseases characterized by diseased cells expressing CLDN18.2 are treatable by a therapy targeting CLDN18.2 such as cancer diseases, in particular those described herein.

In one embodiment of any of the above aspects, the sample, cellular sample or biological sample is from a patient having a cancer disease, being suspected of having or falling ill with a cancer disease or having a potential for a cancer disease. In one embodiment, the sample, cellular sample or biological sample is from a tissue or organ wherein the cells when the tissue or organ is free of cancer do not substantially express CLDN18.2. Preferably said tissue is a tissue other than stomach tissue. Preferably, said tissue is tissue of lung, esophagus, pancreas or breast and the tissue or organ optionally has already been diagnosed as being affected by a cancer disease, e.g. by visual inspection or culture testing of cells of said tissue or organ. In this embodiment, the presence of CLDN18.2 or CLDN18.2-expressing cells and/or a quantity of CLDN18.2 or CLDN18.2-expressing cells which is increased compared to a reference level, e.g. compared to a patient without a tumor disease, may indicate that a patient is suitable for a therapy involving the targeting of cells expressing CLDN18.2.

In one aspect, the invention provides compositions, e.g., diagnostic compositions, or kits, comprising an antibody or antigen-binding fragment or a combination of antibodies and/or or antigen-binding fragments described herein. Such diagnostic compositions or test kits are useful in the methods of the invention such as the methods for diagnosis, detection or monitoring of the invention. These kits may optionally comprise a detectable label, e.g. indicator enzymes, radiolabels, fluorophores, or paramagnetic particles. Kits may include informative pamphlets, for example, pamphlets informing one how to use reagents to practice a method disclosed herein.

Other features and advantages of the instant invention will be apparent from the following detailed description and claims.

BRIEF DESCRIPTION OF THE DRAWINGS

FIG. 1: Sequence alignment of claudin 18 proteins (human/murine)

The sequence alignment shows the high homology between human and mouse claudin 18.2 and human claudin 18.1 and claudin 18.2.

Figure 2:
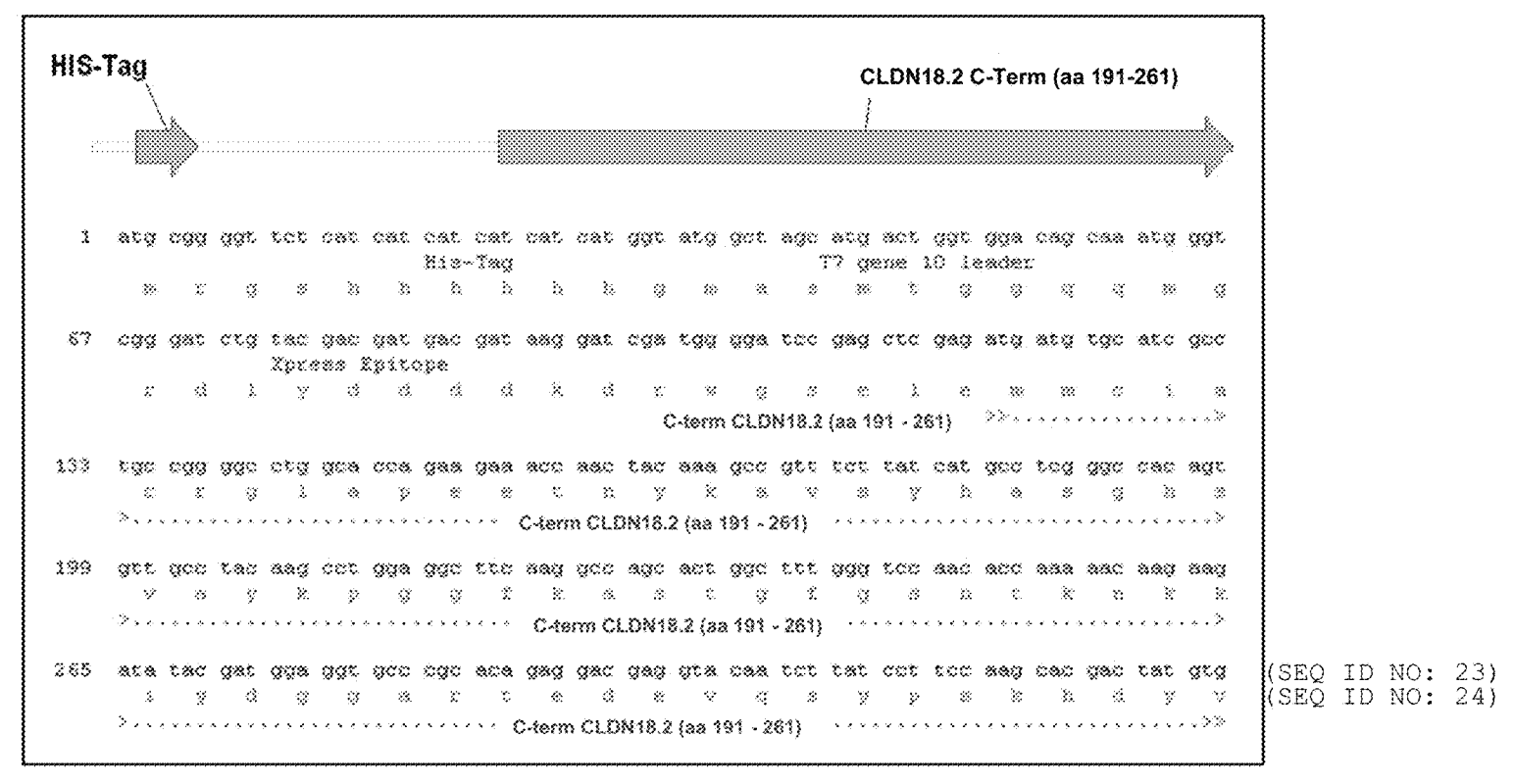

FIG. 2: Recombinant protein including the C-terminal portion of CLDN18.2 (aa191-261) used for immunization of mice FIG. 3: Sequence-analysis of 43-14A and 35-22A antibodies

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, 2nd Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "antigen" relates to an agent comprising an epitope against which an immune response is directed and/or is to be generated. Preferably, an antigen in the context of the present invention is a molecule which, optionally after processing, induces an immune reaction, which is preferably specific for the antigen. The term "antigen" includes in particular proteins, peptides, polysaccharides, nucleic acids, especially RNA and DNA, and nucleotides.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein such as a CLDN preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "discontinuous epitope" as used herein, means a conformational epitope on a protein antigen which is formed from at least two separate regions in the primary sequence of the protein.

In a preferred embodiment, an antigen is a tumor-associated antigen, such as CLDN18.2, i.e., a constituent of cancer cells which may be derived from the cytoplasm, the cell surface and the cell nucleus, in particular those antigens which are produced, preferably in large quantity, intracellular or as surface antigens on cancer cells.

In the context of the present invention, the terms "tumor-associated antigen" or "tumor antigen" relate to proteins that are under normal conditions specifically expressed in a limited number of tissues and/or organs or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably associated with the cell surface of a cancer cell and is preferably not or only rarely expressed in normal tissues. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor-associated antigen is identical between the tumor-associated antigen which is expressed in normal tissues and the tumor-associated antigen which is expressed in cancer tissues.

Examples for differentiation antigens which ideally fulfill the criteria for tumor-associated antigens as target structures in tumor immunotherapy, in particular, in tumor vaccination are the cell surface proteins of the claudin family, such as CLDN18.2. Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm.

The term "claudin 18" or "CLDN18" preferably relates to human CLDN18 and includes any splice variants such as CLDN18.1 and CLDN18.2 of CLDN18. CLDN18.1 and CLDN18.2 differ in the N-terminal portion which comprises the first transmembrane (TM) region and loop1, whereas the primary protein sequence of the C-terminus is identical.

The term "CLDN18.1" preferably relates to human CLDN18.1, and, in particular, to a protein comprising the amino acid sequence according to SEQ ID NO: 1 of the sequence listing or a variant of said amino acid sequence.

The term "CLDN18.2" preferably relates to human CLDN18.2, and, in particular, to a protein comprising the amino acid sequence according to SEQ ID NO: 2 of the sequence listing or a variant of said amino acid sequence.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence.

The terms "CLDN", "CLDN18", "CLDN18.1" and "CLDN18.2" shall encompass any posttranslationally modified variants and conformation variants.

CLDN18.2 is selectively expressed in normal tissues in differentiated epithelial cells of the gastric mucosa. CLDN18.2 is expressed in cancers of various origins, and is particularly suited as target structure for the development of antibody-mediated cancer immunotherapy due to its selective expression (no expression in a toxicity relevant normal tissue) and localization to the plasma membrane. For example, CLDN18.2 has been found to be expressed in pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis. Cells expressing CLDN18.2 are preferably cancer cells and are, in particular, selected from the group consisting of tumorigenic gastric, esophageal, pancreatic, lung, ovarian, colon, hepatic, head-neck, and gallbladder cancer cells.

According to the invention, a cell expressing CLDN18.2 is preferably characterized by cell-surface membrane-bound CLDN18.2, i.e. CLDN18.2 is associated with the cell surface. Furthermore, according to the invention, cellular CLDN18.2 is preferably cell-surface membrane-bound CLDN18.2. A cell expressing CLDN18.2 or a cell characterized by association of CLDN18.2 with its cell surface preferably is a cancer cell, preferably a cancer cell from a cancer described herein.

The term "associated with the cell surface" means that a tumor-associated antigen such as CLDN18.2 is associated with and located at the plasma membrane of a cell, wherein at least a part of the tumor-associated antigen faces the extracellular space of said cell and is accessible from the outside of said cell, e.g., by antibodies located outside the cell. In this context, a part is preferably at least 4, preferably at least 8, preferably at least 12, more preferably at least 20 amino acids. The association may be direct or indirect. For example, the association may be by one or more transmembrane domains, one or more lipid anchors, or by the interaction with any other protein, lipid, saccharide, or other structure that can be found on the outer leaflet of the plasma membrane of a cell. For example, a tumor-associated antigen associated with the surface of a cell may be a transmembrane protein having an extracellular portion or may be a protein associated with the surface of a cell by interacting with another protein that is a transmembrane protein.

"Cell surface" or "surface of a cell" is used in accordance with its normal meaning in the art, and thus includes the outside of the cell which is accessible to binding by proteins and other molecules.

According to the invention CLDN18.2 is not substantially expressed in a cell and is not substantially associated with a cell surface if the level of expression and association exceeds the level of expression and association in non-cancerous tissue other than stomach by no more than 2-fold, preferably 1.5-fold, and preferably does not exceed the level of expression and association in said non-cancerous tissue. Preferably, CLDN18.2 is not substantially expressed in a cell and is not substantially associated with a cell surface if the level of expression or association is below the detection limit and/or if the level of expression or association is too low to allow binding by CLDN18.2-specific antibodies added to the cells.

According to the invention CLDN18.2 is expressed in a cell and is associated with a cell surface if the level of expression and association exceeds the level of expression and association in non-cancerous tissue other than stomach, preferably by more than 2-fold, preferably 10-fold, 100-fold, 1000-fold, or 10000-fold. Preferably, CLDN18.2 is expressed in a cell and is associated with a cell surface if the level of expression and association is above the detection limit and/or if the level of expression and association is high enough to allow binding by CLDN18.2-specific antibodies added to the cells.

The term "antibody" refers to a glycoprotein comprising at least two heavy (H) chains and two light (L) chains inter-connected by disulfide bonds, and includes any molecule comprising an antigen binding portion thereof. The term "antibody" includes monoclonal antibodies and fragments or derivatives of antibodies, including, without limitation, human antibodies, humanized antibodies, chimeric antibodies, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives as described herein. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The antibodies described herein may be human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically, the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

The terms "antigen-binding portion" of an antibody (or simply "binding portion") or "antigen-binding fragment" of an antibody (or simply "binding fragment") refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The antibodies described herein may be monoclonal antibodies. The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The antibodies described herein may be recombinant antibodies. The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The invention includes all antibodies and derivatives of antibodies as described herein which for the purposes of the invention are encompassed by the term "antibody". The term "antibody derivatives" refers to any modified form of an antibody, e.g., a conjugate of the antibody and another agent or antibody, or an antibody fragment.

The antibodies described herein are preferably isolated. An "isolated antibody" as used herein, is intended to refer to an antibody which is substantially free of other antibodies having different antigenic specificities. Moreover, an isolated antibody may be substantially free of other cellular material and/or chemicals.

According to the present invention, an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An antibody is not (substantially) capable of binding to a target if it has no significant affinity for said target and does not bind significantly, in particular does not bind detectably, to said target in standard assays. Preferably, the antibody does not detectably bind to said target if present in a concentration of up to 2, preferably 10, more preferably 20, in particular 50 or 100 µg/ml or higher. Preferably, an antibody has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the antibody is capable of binding. For example, if the $K_D$ for binding of an antibody to the target to which the antibody is capable of binding is $10^{-7}$ M, the $K_D$ for binding to a target for which the antibody has no significant affinity would be is at least $10^{-6}$ M, $10^{-5}$ M, $10^{-4}$ M, $10^{-3}$ M, $10^{-2}$ M, or $10^{-1}$ M.

An antibody is specific for a predetermined target if it is capable of binding to said predetermined target while it is not capable of binding to other targets, i.e. has no significant affinity for other targets and does not significantly bind to other targets in standard assays. According to the invention, an antibody is specific for CLDN18.2 if it is capable of binding to CLDN18.2 but is not (substantially) capable of binding to other targets, in particular proteins other than claudin proteins, preferably proteins other than CLDN18, in particular proteins other than CLDN18.2. Preferably, an antibody is specific for CLDN18.2 if the affinity for and the binding to such other targets does not significantly exceed the affinity for or binding to claudin-unrelated proteins such as bovine serum albumin (BSA), casein, human serum albumin (HSA) or non-claudin transmembrane proteins such as MHC molecules or transferrin receptor or any other specified polypeptide. Preferably, an antibody is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an antibody to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an antibody to a target can be determined experimentally using any suitable method; see, for example, Berzofsky et al., "Antibody-Antigen Interactions" In Fundamental Immunology, Paul, W. E., Ed., Raven Press New York, N.Y. (1984), Kuby, Janis Immunology, W. H. Freeman and Company New York, N.Y. (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

As used herein, "isotype" refers to the antibody class (e.g., IgM or IgG1) that is encoded by heavy chain constant region genes. Antibodies according to the invention include polyclonal and monoclonal antibodies and include IgG2a (e.g. IgG2a, κ, λ), IgG2b (e.g. IgG2b, κ, λ), IgG3 (e.g. IgG3, κ, λ) and IgM antibodies. However, other antibody isotypes are also encompassed by the invention, including IgG1, IgA1, IgA2, secretory IgA, IgD, and IgE antibodies.

As used herein, "isotype switching" refers to the phenomenon by which the class, or isotype, of an antibody changes from one Ig class to one of the other Ig classes.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

According to the invention, antibodies may be derived from different species, including but not limited to mouse, rat, rabbit, guinea pig and human. Antibodies also include chimeric molecules in which an antibody constant region derived from one species, preferably human, is combined with the antigen binding site derived from another species. Moreover, antibodies include humanized molecules in which the antigen binding sites of an antibody derived from a non-human species are combined with constant and framework regions of human origin.

Antibodies can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies directed against CLDN18.2 can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607

Yet another strategy for generating monoclonal antibodies is to directly isolate genes encoding antibodies from lymphocytes producing antibodies of defined specificity; see e.g. Babcock et al., 1996; A novel strategy for generating monoclonal antibodies from single, isolated lymphocytes producing antibodies of defined specificities. For details of recombinant antibody engineering see also Welschof and Kraus, Recombinant antibodes for cancer therapy ISBN-0-89603-918-8 and Benny K. C. Lo Antibody Engineering ISBN 1-58829-092-1.

To generate antibodies to CLDN18.2, mice can be immunized with carrier-conjugated peptides derived from the CLDN18.2 sequence, an enriched preparation of recombinantly expressed CLDN18.2 antigen or fragments thereof and/or cells expressing CLDN18.2 or fragments thereof, as described. Alternatively, mice can be immunized with DNA encoding full length human CLDN18.2 or fragments thereof. In the event that immunizations using a purified or enriched preparation of the CLDN18.2 antigen do not result in antibodies, mice can also be immunized with cells expressing CLDN18.2, e.g., a cell line, to promote immune responses.

The immune response can be monitored over the course of the immunization protocol with plasma and serum samples being obtained by tail vein or retroorbital bleeds. Mice with sufficient titers of anti-CLDN18.2 immunoglobulin can be used for fusions. Mice can be boosted intraperitonealy or intravenously with CLDN18.2 expressing cells 3-5 days before sacrifice and removal of the spleen to increase the rate of specific antibody secreting hybridomas.

To generate hybridomas producing monoclonal antibodies to CLDN18.2, cells from lymph nodes, spleens or bone marrow obtained from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using CLDN18.2 expressing cells, antibodies with specificity for CLDN18.2 can be identified. The antibody secreting hybridomas can be replated, screened again, and if still positive for anti-CLDN18.2 monoclonal antibodies can be subcloned by limiting dilution. The stable subclones can then be cultured in vitro to generate antibody in tissue culture medium for characterization.

Antibodies of the invention can also be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. *E. coli*. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Chimeric antibodies are antibodies, the different portions of which are derived from different animal species, such as those having a variable region derived from a murine antibody and a human immunoglobulin constant region. Chimerisation of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment, chimeric antibodies are generated by joining human kappa-light chain constant region to murine light chain variable region. In an also preferred embodiment, chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A. 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual positions evenly across the variable region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see WO 99/45962). Partial heavy and light chain sequences spanning the CDR regions are typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas may be used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266: 19867-19870); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed chimerized or humanized heavy and light chain variable regions are then combined with cloned promoter, leader, translation initiation, constant region, 3' untranslated, polyadenylation, and transcription termination sequences to form expression vector constructs. The heavy and light chain expression constructs can be combined into a single vector, co-transfected, serially transfected, or separately transfected into host cells which are then fused to form a host cell expressing both chains. Plasmids for use in construction of expression vectors for human IgGκ are described. The plasmids can be constructed so that PCR amplified V heavy and V kappa light chain cDNA sequences can be used to reconstruct complete heavy and light chain minigenes. These plasmids can be used to express completely human, or chimeric IgG1, Kappa or IgG4, Kappa antibodies. Similar plasmids can be constructed for expression of other heavy chain isotypes, or for expression of antibodies comprising lambda light chains.

Thus, in another aspect of the invention, the structural features of the anti-CLDN18.2 antibodies described herein, are used to create structurally related humanized anti-CLDN18.2 antibodies that retain at least one functional property of the antibodies of the invention, such as binding to CLDN18.2. More specifically, one or more CDR regions of mouse monoclonal antibodies can be combined recombinantly with known human framework regions and CDRs to create additional, recombinantly-engineered, humanized anti-CLDN18.2 antibodies.

The ability of an antibody to bind CLDN18.2 can be determined using standard binding assays, e.g., ELISA, Western Blot, Immunofluorescence and Flow cytometric analysis.

ELISA can be used to demonstrate the presence of antibodies in sera of immunized mice or binding of monoclonal antibodies to CLDN18.2 protein or peptides. Peptides or protein used for immunization may be used for determining the specificity of hybridoma supernatants or analysing serum titers.

In order to demonstrate presence of antibodies in sera of immunized mice or binding of monoclonal antibodies to living cells, flow cytometry can be used. Cell lines expressing naturally or after transfection antigen and negative controls lacking antigen expression (grown under standard growth conditions) can be mixed with various concentrations of monoclonal antibodies in hybridoma supernatants or in PBS containing 1% FBS, and can be incubated at 4° C. for 30 min. After washing, the APC- or Alexa647-labeled anti IgG antibody can bind to antigen-bound monoclonal antibody under the same conditions as the primary antibody staining. The samples can be analyzed by flow cytometry with a FACS instrument using light and side scatter properties to gate on single, living cells. In order to distinguish antigen-specific monoclonal antibodies from non-specific binders in a single measurement, the method of co-transfection can be employed. Cells transiently transfected with plasmids encoding antigen and a fluorescent marker can be stained as described above. Transfected cells can be detected in a different fluorescence channel than antibody-stained cells. As the majority of transfected cells express both transgenes, antigen-specific monoclonal antibodies bind preferentially to fluorescence marker expressing cells, whereas non-specific antibodies bind in a comparable ratio to non-transfected cells. An alternative assay using fluorescence microscopy may be used in addition to or instead of the flow cytometry assay. Cells can be stained exactly as described above and examined by fluorescence microscopy.

In order to demonstrate presence of anti-CLDN18.2 antibodies in sera of immunized mice or binding of monoclonal antibodies to living cells expressing CLDN18.2, immunofluorescence microscopy analysis can be used. For example, cell lines expressing either spontaneously or after transfection CLDN18.2 and negative controls lacking CLDN18.2 expression are grown in chamber slides under standard growth conditions in DMEM/F12 medium, supplemented with 10% fetal calf serum (FCS), 2 mM L-glutamine, 100 IU/ml penicillin and 100 µg/ml streptomycin. Cells can then be fixed with methanol or paraformaldehyde or left untreated. Cells can then be reacted with monoclonal antibodies against CLDN18.2 for 30 min. at 25° C. After washing, cells can be reacted with an Alexa555-labelled anti-mouse IgG secondary antibody (Molecular Probes) under the same conditions. Cells can then be examined by fluorescence microscopy.

Total CLDN18.2 levels in cells can be observed when cells are methanol fixed or paraformaldehyde fixed and permeabilized with Triton X-100. In living cells and non-permeabilized, paraformaldehyde fixed cells surface localization of CLDN18.2 can be examined. Additionally targeting of CLDN18.2 to tight junctions can be analyzed by co-staining with tight junction markers such as ZO-1. Furthermore, effects of antibody binding and CLDN18.2 localization within the cell membrane can be examined.

Anti-CLDN18.2 IgG can be further tested for reactivity with CLDN18.2 antigen by Western Blotting. Briefly, cell extracts from cells expressing CLDN18.2 and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Anti-CLDN18.2 mouse IgGs can be further tested for reactivity with CLDN18.2 antigen by Immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection with CLDN18.2. For immunostaining, antibodies reactive to CLDN18.2 can be incubated followed by horseradish-peroxidase conjugated goat anti-mouse or goat anti-rabbit antibodies according to the vendors instructions.

One particularly preferred methodology for assaying CLDN18.2 in the methods of the invention is Immunohistochemistry or IHC. Immunohistochemistry or IHC refers to the process of detecting antigens (e.g., proteins) in cells of a tissue section, e.g. cells of the tissues mentioned herein. Immunohistochemical staining is widely used in the diagnosis of abnormal cells such as those found in cancerous tumors. Visualising an antibody-antigen interaction can be accomplished in a number of ways. In the most common instance, an antibody is conjugated to an enzyme, such as peroxidase, that can catalyse a colour-producing reaction. Alternatively, the antibody can also be tagged to a fluorophore, such as fluorescein or rhodamine.

Preparation of the sample is critical to maintain cell morphology, tissue architecture and the antigenicity of target epitopes. This requires proper tissue collection, fixation and sectioning. Paraformaldehyde is usually used with fixation. Depending on the purpose and the thickness of the experimental sample, either thin (about 4-40 μm) sections are sliced from the tissue of interest, or if the tissue is not very thick and is penetrable it is used whole. The slicing is usually accomplished through the use of a microtome, and slices are mounted on slides.

The sample may require additional steps to make the epitopes available for antibody binding, including deparaffinization and antigen retrieval. Detergents like Triton X-100 are generally used in Immunohistochemistry to reduce surface tension, allowing less reagent to be used to achieve better and more even coverage of the sample.

The direct method of immunohistochemical staining uses one labelled antibody, which binds directly to the antigen being stained for. The indirect method of immunohistochemical staining which is more common uses one antibody against the antigen being probed for, and a second, labelled, antibody against the first.

To reduce background staining in IHC, the samples are incubated with a buffer that blocks the reactive sites to which the primary or secondary antibodies may otherwise bind. Primary antibodies are raised against an antigen of interest and are typically unconjugated (unlabelled), while secondary antibodies are raised against immunoglobulins of the primary antibody species. The secondary antibody is usually conjugated to a linker molecule, such as biotin, that then recruits reporter molecules, or the secondary antibody is directly bound to the reporter molecule itself. Common blocking buffers include normal serum, non-fat dry milk, BSA or gelatin, and commercial blocking buffers.

Reporter molecules vary based on the nature of the detection method, and the most popular methods of detection are with enzyme- and fluorophore-mediated chromogenic and fluorescence detection, respectively. With chromogenic reporters, an enzyme label is reacted with a substrate to yield an intensely colored product that can be analyzed with an ordinary light microscope. While the list of enzyme substrates is extensive, alkaline phosphatase (AP) and horseradish peroxidase (HRP) are the two enzymes used most extensively as labels for protein detection. An array of chromogenic, fluorogenic and chemiluminescent substrates is available for use with either enzyme, including DAB or BCIP/NBT. Fluorescent reporters are small, organic molecules used for IHC detection. For chromogenic and fluorescent detection methods, densitometric analysis of the signal can provide semi- and fully-quantitative data, respectively, to correlate the level of reporter signal to the level of protein expression or localization.

After immunohistochemical staining of the target antigen, a second stain is often applied to provide contrast that helps the primary stain stand out. Many of these stains show specificity for discrete cellular compartments or antigens, while others will stain the whole cell. Both chromogenic and fluorescent dyes are available for IHC to provide a vast array of reagents to fit every experimental design. Hematoxylin, Hoechst stain and DAPI are commonly used.

Mapping of epitopes recognized by antibodies can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

The term "immune effector functions" in the context of the present invention includes any functions mediated by components of the immune system that result in the inhibition of tumor growth and/or inhibition of tumor development, including inhibition of tumor dissemination and metastasis. Preferably, immune effector functions result in killing of cancer cells. Preferably, the immune effector functions in the context of the present invention are antibody-mediated effector functions. Such functions comprise complement dependent cytotoxicity (CDC), antibody-dependent cell-mediated cytotoxicity (ADCC), antibody-dependent cell-mediated phagocytosis (ADCP), induction of apoptosis in the cells carrying the tumor-associated antigen, for example, by binding of the antibody to a surface antigen, inhibition of CD40L-mediated signal transduction, for example, by binding of the antibody to the CD40 receptor or CD40 ligand (CD40L), and/or inhibition of proliferation of the cells carrying the tumor-associated antigen, preferably ADCC and/or CDC. Thus, antibodies that are capable of mediating one or more immune effector functions are preferably able to mediate killing of cells by inducing CDC-mediated lysis, ADCC-mediated lysis, apoptosis, homotypic adhesion, and/or phagocytosis, preferably by inducing CDC-mediated lysis and/or ADCC-mediated lysis. Antibodies may also exert an effect simply by binding to tumor-associated antigens on the surface of a cancer cell. For example, antibodies may block the function of the tumor-associated antigen or induce apoptosis just by binding to the tumor-associated antigen on the surface of a cancer cell.

ADCC describes the cell-killing ability of effector cells, in particular lymphocytes, which preferably requires the target cell being marked by an antibody. ADCC preferably occurs when antibodies bind to antigens on cancer cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that also leads to antigen presentation and the induction of tumor-directed T-cell responses. Preferably, in vivo induction of ADCC will lead to tumor-directed T-cell responses and further host-derived antibody responses.

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple Clq binding sites in close proximity on the $C_H2$ domains of participating antibody molecules such as IgG molecules (Clq is one of three subcomponents of complement C1). Preferably these uncloaked Clq binding sites convert the previously low-affinity Clq-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell and may lead to apoptosis.

The term "immune effector cells" in the context of the present invention relates to cells which exert effector functions during an immune reaction. For example, such cells secrete cytokines and/or chemokines, kill microbes, secrete antibodies, recognize cancerous cells, and optionally eliminate such cells. For example, immune effector cells comprise T-cells (cytotoxic T-cells, helper T-cells, tumor infiltrating T-cells), B-cells, natural killer cells, neutrophils, macrophages, and dendritic cells.

A nucleic acid is according to the invention preferably deoxyribonucleic acid (DNA) or ribonucleic acid (RNA), more preferably RNA, most preferably in vitro transcribed RNA (IVT RNA). Nucleic acids include according to the invention genomic DNA, cDNA, mRNA, recombinantly prepared and chemically synthesized molecules. A nucleic acid may according to the invention be in the form of a molecule which is single stranded or double stranded and linear or closed covalently to form a circle. A nucleic can be employed for introduction into, i.e. transfection of, cells, for example, in the form of RNA which can be prepared by in vitro transcription from a DNA template. The RNA can moreover be modified before application by stabilizing sequences, capping, and polyadenylation.

The nucleic acids described herein may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

As the vector for expression of an antibody, either of a vector type in which the antibody chains are present in different vectors or a vector type in which the antibody chains are present in the same vector can be used.

As used herein, the term "RNA" means a molecule comprising at least one ribonucleotide residue. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region, a protein or peptide coding region and a 3' non translated region. mRNA has a limited halftime in cells and in vitro.

In the context of the present invention, the term "transcription" relates to a process, wherein the genetic code in a DNA sequence is transcribed into RNA.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid. The term "homologous" means that the nucleic acids are also functionally linked naturally and the term "heterologous" means that the nucleic acids are not functionally linked naturally.

A nucleic acid and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" or "expression control element" comprises according to the invention promoters, ribosome binding sites, enhancers and other control elements which regulate transcription of a gene or translation of a mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

According to the invention the term "promoter" or "promoter region" relates to a nucleic acid sequence which is located upstream (5') to the nucleic acid sequence being expressed and controls expression of the sequence by providing a recognition and binding site for RNA-polymerase. The "promoter region" may include further recognition and binding sites for further factors which are involved in the regulation of transcription of a gene. A promoter may control the transcription of a prokaryotic or eukaryotic gene. Furthermore, a promoter may be "inducible" and may initiate transcription in response to an inducing agent or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g. human GAPDH (glyceraldehyde-3-phosphate dehydrogenase), and including or not including (an) additional intron(s).

The term "expression" is used herein in its broadest meaning and comprises the production of RNA or of RNA and protein or peptide. With respect to RNA, the term "expression" or "translation" relates in particular to the production of peptides or proteins. Expression may be transient or may be stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor-associated antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor-associated antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue is specifically expressed in cells of the gastric mucosa. In some embodiments, a tumor-associated antigen may also be specifically expressed under normal conditions in more than one tissue type or organ, such as in 2 or 3 tissue types or organs, but preferably in not more than 3 different tissue or organ types. In this case, the tumor-associated antigen is then specifically expressed in these organs.

The term "translation" according to the invention relates to the process in the ribosomes of a cell by which a strand of messenger RNA directs the assembly of a sequence of amino acids to make a protein or peptide.

According to the invention, the term "nucleic acid encoding" means that nucleic acid, if present in the appropriate environment, preferably within a cell, can be expressed to produce a protein or peptide it encodes.

The term "peptide" comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

Preferably, the proteins and peptides described according to the invention have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo.

The teaching given herein with respect to specific amino acid sequences, e.g. those shown in the sequence listing, is to be construed so as to also relate to modifications, i.e. variants, of said specific sequences resulting in sequences which are functionally equivalent to said specific sequences, e.g. amino acid sequences exhibiting properties identical or similar to those of the specific amino acid sequences. One important property is to retain binding of an antibody to its target. Preferably, a sequence modified with respect to a specific sequence, when it replaces the specific sequence in an antibody retains binding of said antibody to the target.

It will be appreciated by those skilled in the art that in particular the sequences of the CDR sequences, hypervariable and variable regions can be modified without losing the ability to bind to a target. For example, CDR sequences will be either identical or highly homologous to the CDR sequences specified herein.

By "highly homologous" it is contemplated that from 1 to 5, preferably from 1 to 4, such as 1 to 3 or 1 or 2 substitutions may be made.

The term "variant" according to the invention also includes mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the invention at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing proteins and peptides having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

The invention includes derivatives of the peptides or proteins described herein which are comprised by the terms "peptide" and "protein". According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. In one embodiment, "derivatives" of proteins or peptides include those modified analogs resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. The term "derivative" also extends to all functional chemical equivalents of said proteins and peptides. Preferably, a modified peptide has increased stability and/or increased immunogenicity.

According to the invention, a variant, derivative, modified form, fragment, part or portion of an amino acid sequence, peptide or protein preferably has a functional property of the amino acid sequence, peptide or protein, respectively, from which it has been derived, i.e. it is functionally equivalent. In one embodiment, a variant, derivative, modified form, fragment, part or portion of an amino acid sequence, peptide or protein is immunologically equivalent to the amino acid sequence, peptide or protein, respectively, from which it has been derived. In one embodiment, the functional property is an immunological property.

The term "derived" means according to the invention that a particular entity, in particular a particular sequence, is present in the object from which it is derived, in particular an organism or molecule. In the case of amino acid sequences, especially particular sequence regions, "derived" in particular means that the relevant amino acid sequence is derived from an amino acid sequence in which it is present.

The term "cell" or "host cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. The term "cell" includes according to the invention prokaryotic cells (e.g., E. coli) or eukaryotic cells (e.g., dendritic cells, B cells, CHO cells, COS cells, K562 cells, HEK293 cells, HELA cells, yeast cells, and insect cells). Mammalian cells are particularly preferred, such as cells from humans, mice, hamsters, pigs, goats, and primates. The cells may be derived from a large number of tissue types and include primary cells and cell lines. The term "cell" includes non-cancerous cells and cancer cells such as cells of the cancer types disclosed herein.

A cell which comprises a nucleic acid molecule preferably express the peptide or protein encoded by the nucleic acid.

"Target cell" shall mean a cell which is a target for an immune response such as an antibody. Target cells include any undesirable cell such as a cancer cell as described herein. In preferred embodiments, the target cell is a cell expressing CLDN18.2. Cells expressing CLDN18.2 typically include cancer cells.

The terms "transgenic animal" refers to an animal having a genome comprising one or more transgenes, preferably antibody heavy and/or light chain transgenes, or transchromosomes (either integrated or non-integrated into the animal's natural genomic DNA) and which is preferably capable of expressing the transgenes. For example, a transgenic mouse can have a human light chain transgene and either a human heavy chain transgene or human heavy chain transchromosome, such that the mouse produces human anti-CLDN18.2 antibodies when immunized with CLDN18.2 antigen and/or cells expressing CLDN18.2. The human heavy chain transgene can be integrated into the chromosomal DNA of the mouse, as is the case for transgenic mice, e.g., HuMAb mice, such as HCo7 or HCo12 mice, or the human heavy chain transgene can be maintained extrachromosomally, as is the case for transchromosomal (e.g., KM) mice as described in WO 02/43478. Such transgenic and transchromosomal mice may be capable of producing multiple isotypes of human monoclonal antibodies to CLDN18.2 (e.g., IgG, IgA and/or IgE) by undergoing V-D-J recombination and isotype switching.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral immune reaction, the strength and/or duration of the induced immune reaction, or the specificity of the immune reaction. In the context of the present invention, the term "immunologically equivalent" is preferably used with respect to the immunological effects or properties of a peptide or peptide variant used for immunization or an antibody. A particular immunological property is the ability to bind to antibodies and, where appropriate, generate an immune response, preferably by stimulating the generation of antibodies. For example, an amino acid sequence is immunologically equivalent to a reference amino acid sequence if said amino acid sequence when exposed to the immune system of a subject induces an immune reaction, preferably antibodies, having a specificity of reacting with the reference amino acid sequence, such as the reference amino acid sequence forming part of CLDN18.2.

The invention provides methods for detecting the presence of CLDN18.2 antigen in a sample, or measuring the amount of CLDN18.2 antigen, comprising contacting the sample, and optionally a control sample, with an antibody of the invention which binds to CLDN18.2, under conditions that allow for formation of a complex between the antibody and CLDN18.2. The formation of a complex is then detected, wherein a difference in complex formation between the sample compared to a control sample is indicative for the presence of CLDN18.2 antigen in the sample.

Methods as described above are useful, in particular, for diagnosing CLDN18.2-related diseases such as cancer diseases. Preferably an amount of CLDN18.2 in a sample which is higher than the amount of CLDN18.2 in a reference or control sample is indicative for the presence of a CLDN18.2-related disease in a subject, in particular a human, from which the sample is derived.

When used in methods as described above, an antibody described herein may be provided with a label that functions to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc.

Labels comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium.

According to the invention, a "reference" such as a reference sample or reference organism may be used to correlate and compare the results obtained in the methods of the invention from a test sample or test organism. Typically the reference organism is a healthy organism, in particular an organism which does not suffer from a disease such as a cancer disease. A "reference value" or "reference level" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

"Reduce" or "inhibit" as used herein means the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%.

The agents, compositions and methods described herein can be used to diagnose a subject with a disease. Diseases which can be diagnosed encompass all diseases expressing CLDN18.2. Particularly preferred diseases are cancer diseases such as cancer diseases described herein.

According to the invention, the term "disease" refers to any pathological state, including cancer diseases, in particular those forms of cancer diseases described herein.

The term "normal" such as used in the terms "normal tissue" or "normal conditions" refers to healthy tissue or the conditions in a healthy subject, i.e., non-pathological conditions, wherein "healthy" preferably means non-cancerous.

"Disease involving cells expressing CLDN18.2" means according to the invention that expression of CLDN18.2 in cells of a diseased tissue or organ is preferably increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving or being associated with cells expressing CLDN18.2 include cancer diseases, in particular those forms of cancer described herein.

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

A benign tumor is a tumor that lacks all three of the malignant properties of a cancer. Thus, by definition, a benign tumor does not grow in an unlimited, aggressive manner, does not invade surrounding tissues, and does not spread to non-adjacent tissues (metastasize). Common examples of benign tumors include moles and uterine fibroids.

The term "benign" implies a mild and nonprogressive disease, and indeed, many kinds of benign tumors are harmless to the health. However, some neoplasms which are defined as "benign tumors" because they lack the invasive properties of a cancer, may still produce negative health effects. Examples of this include tumors which produce a "mass effect" (compression of vital organs such as blood vessels), or "functional" tumors of endocrine tissues, which may overproduce certain hormones (examples include thyroid adenomas, adrenocortical adenomas, and pituitary adenomas).

Benign tumors typically are surrounded by an outer surface that inhibits their ability to behave in a malignant manner. In some cases, certain "benign" tumors may later give rise to malignant cancers, which result from additional genetic changes in a subpopulation of the tumor's neoplastic cells. A prominent example of this phenomenon is the tubular adenoma, a common type of colon polyp which is an important precursor to colon cancer. The cells in tubular adenomas, like most tumors which frequently progress to cancer, show certain abnormalities of cell maturation and appearance collectively known as dysplasia. These cellular abnormalities are not seen in benign tumors that rarely or never turn cancerous, but are seen in other pre-cancerous tissue abnormalities which do not form discrete masses, such as pre-cancerous lesions of the uterine cervix. Some authorities prefer to refer to dysplastic tumors as "pre-malignant", and reserve the term "benign" for tumors which rarely or never give rise to cancer.

Neoplasm is an abnormal mass of tissue as a result of neoplasia. Neoplasia (new growth in Greek) is the abnormal proliferation of cells. The growth of the cells exceeds, and is uncoordinated with that of the normal tissues around it. The growth persists in the same excessive manner even after cessation of the stimuli. It usually causes a lump or tumor. Neoplasms may be benign, pre-malignant or malignant.

"Growth of a tumor" or "tumor growth" according to the invention relates to the tendency of a tumor to increase its size and/or to the tendency of tumor cells to proliferate.

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not. According to the invention, the terms "cancer" and "tumor" or "cancer disease" and "tumor disease" are generally used interchangeably herein to refer to diseases wherein cells display an uncontrolled growth and optionally invasion and/or metastasis.

Preferably, a "cancer disease" according to the invention is characterized by cells expressing CLDN18.2. A cell expressing CLDN18.2 preferably is a cancer cell, preferably of the tumors and cancers described herein. Preferably, such cell is a cell other than a stomach cell.

Cancers are classified by the type of cell that resembles the tumor and, therefore, the tissue presumed to be the origin of the tumor. These are the histology and the location, respectively.

The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

The main types of lung cancer are small cell lung carcinoma (SCLC) and non-small cell lung carcinoma (NSCLC). There are three main sub-types of the non-small cell lung carcinomas: squamous cell lung carcinoma, adenocarcinoma, and large cell lung carcinoma. Adenocarcinomas account for approximately 10% of lung cancers. This cancer usually is seen peripherally in the lungs, as opposed to small cell lung cancer and squamous cell lung cancer, which both tend to be more centrally located.

According to the invention, a "carcinoma" is a malignant tumor derived from epithelial cells. This group represents the most common cancers, including the common forms of breast, prostate, lung and colon cancer.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

A relapse or recurrence occurs when a person is affected again by a condition that affected them in the past. For example, if a patient has suffered from a cancer disease, has received a successful treatment of said disease and again develops said disease said newly developed disease may be considered as relapse or recurrence. However, according to the invention, a relapse or recurrence of a cancer disease may but does not necessarily occur at the site of the original cancer disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

By "treat" is meant to administer a compound or composition to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

By "being at risk" is meant a subject, i.e. a patient, that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases.

The term "immunotherapy" relates to a treatment involving a specific immune reaction. In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor. Immunotherapy may be performed using any of a variety of techniques, in which agents function to remove antigen-expressing cells from a patient.

Within certain embodiments, immunotherapy may be active immunotherapy, in which treatment relies on the in vivo stimulation of the endogenous host immune system to react against diseased cells with the administration of immune response-modifying agents (such as immunoreactive peptides and nucleic acids).

Within other embodiments, immunotherapy may be passive immunotherapy, in which treatment involves the delivery of agents with established tumor-immune reactivity (such as antibodies) that can directly or indirectly mediate antitumor effects and does not necessarily depend on an intact host immune system.

The term "in vivo" relates to the situation in a subject.

The terms "subject", "individual", "organism" or "patient" are used interchangeably and relate to vertebrates, preferably mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans. The term "subject" may also include a patient, i.e., an animal, preferably a human having a disease, preferably a disease as described herein.

According to the invention, a "sample" may be any sample useful according to the present invention, in particular a biological sample such a tissue sample, including body fluids, and/or a cellular sample and may be obtained in the conventional manner such as by tissue biopsy, including punch biopsy, and by taking blood, bronchial aspirate, sputum, urine, feces or other body fluids. According to the invention, the term "sample" also includes processed samples such as fractions or isolates of biological samples, e.g. nucleic acid and peptide/protein isolates. Preferably a sample contains cells or tissue of the organ which is to be examined, e.g. which is to be diagnosed for cancer. For example, if the cancer to be diagnosed is lung cancer a sample may contain cells or tissue obtained from lung.

According to the invention a sample may be a sample such as a bodily sample derived from a patient containing or being expected of containing tumor or cancer cells. The bodily sample may be any tissue sample such as blood, a tissue sample obtained from the primary tumor or from tumor metastases or any other sample containing tumor or cancer cells.

The present invention is described in detail by the figures and examples below, which are used only for illustration purposes and are not meant to be limiting. Owing to the description and the examples, further embodiments which are likewise included in the invention are accessible to the skilled worker.

EXAMPLES

The techniques and methods used herein are described herein or carried out in a manner known per se and as described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information unless specifically indicated.

Example 1: Generation of Monoclonal Antibodies

The aim of this project was to generate murine monoclonal CLDN18-specific antibodies capable of detecting CLDN18.2 expressing tumor cells in stomach CA, esophagus CA, pancreas CA and lung CA FFPE tissues.

To generate a highly specific, high affinity diagnostic CLDN18.2 antibody it was essential to start immunization protocols with a big variation of different immunogens and adjuvants. During the project about 100 mice (C57Bl/6 and Balb/c) were inoculated, using various immunization strategies to trigger an α-CLDN18 immune response.

To trigger the mouse immune system and to overcome the immune tolerance we used virus-like-particles (VLP), peptide-conjugates and recombinant proteins coding for different parts of human CLDN18.2 expressed as recombinant fusion proteins with different expression partners (tags).

Out of 13 different immunization strategies the best results were achieved by treating mice with HIS-tagged CLDN18 C-termal recombinant protein (see FIG. 2; Immunization #20) in combination with various adjuvants (see Table 1, below, fusion 35).

One candidate (35-22A) resulted from a 4 step-immunization strategy (30 days). A further candidate (43-14A) was generated following a 7-step-immunization protocol (79 days)(see Table 1, below, fusion 43).

Two days before splenectomy, the mice were boosted to activate the targeted B-cells.

On the day of fusion the mouse splenocytes were isolated and fused to a mouse myeloma cell line Ag8.653. For fusion of mouse cells to the myeloma we followed the standard protocol published by Köhler and Milstein 1975. After HAT selection supernatants were tested in ELISA for secretion of antibodies recognizing the antigen used for immunizations.

The hybridoma cells of ELISA positive supernatants were subcloned to generate monoclonal hybridomas and supernatants of the subcloned hybridoma cells were rescreened in ELISA. Hybridoma cells of positive clones were expanded and supernatants analyzed further.

Example 2: Western Blot Screen of Monoclonal Hybridoma Supernatants

To answer the question if ELISA-positive antibodies in the supernatants are able to bind to either recombinant claudin 18 or protein lysates from stable transfected claudin 18 expressing HEK293 cells Western Blot-analysis was performed. Antibodies which were able to bind specifically to claudin 18 in a Western Blot-analysis were expanded. Cells were cryoconserved and antibodies purified via MAB-select (FPLC). The antibodies selected by the Western Blot screening were purified and evaluated for their ability to bind their antigen in formalin fixed paraffin-embedded tissues (FFPE) by immunohistochemistry.

Example 3: Histological Analysis—First Screen of Western Blot Positive Antibodies The aim of this experiment was to check the CLDN18 specificity and sensitivity of the antibodies. This was done by using CLDN18 expressing FFPE normal stomach tissue.

In a first experiment the Western Blot tested purified antibodies were analyzed at a concentration of 0.5 µg/ml on human stomach FFPE sections. Antibodies which performed well and did not produce high amounts of background were further titrated to 0.2 & 0.1 µg/ml on various normal stomach tissues to test the sensitivity and specificity. In later development stages the freshly generated antibodies were directly tested at a concentration of 0.2 µg/ml because the best antibody already performed very well at 0.2 µg/ml and did serve as a benchmark. Antibodies generating strong signals on the mucosa epithelium of the tested human stomach tissues and no background on the adjacent mucosa tissues were selected for further titration experiments and specificity analysis. Two antibodies did perform outstanding: 35-22A and 43-14A; see Tables 2 and 3, below.

Antibodies producing strong signals on the tested normal stomach tissue were further analyzed on cancer tissues. The corresponding hybridoma cells were adapted to serum free media. The signals produced using mumAb 43-14A were slightly stronger than the signals produced using mumAb 35-22A; see Table 4, below.

Example 4: Histological in Depth Analysis and Antibody Characterization

The serum free produced antibodies were used to stain stomach CA tissue microarrays (TMA). The amount of stained cases, the strength of the signal and the amount of positive tumor cells were analyzed.

The staining intensities of the mumAbs 35-22A and 43-14A were excellent. No significant differences in the staining pattern and only slight differences in the staining intensities between the tested antibodies 35-22A and 43-14A were detected.

Example 5: Analysis of Antibody Specificity Using a Normal Tissue Panel

The selected antibodies were tested on various, relevant normal tissues to ensure the high CLDN18 target specificity; see Tables 5A and 5B, below.

No significant differences in the staining pattern and staining intensities of the antibodies 35-22A and 43-14A were visible in the previous experiments. Therefore the antibodies were subjected to staining experiments with a more clinically oriented protocol. To simulate the staining processes applied in standard pathology labs a One-Day-Protocol with a short (1 hour) primary antibody incubation step was established.

In all analyzed cases mumAb 43-14A performed extremely good and even better compared to mumAb 35-22A; see Table 6, below.

Example 6: In Depth Analysis on Relevant Tissue—Respiratory Epithelium mumAb 43-14A was additionally analyzed on various relevant respiratory tissues to ensure its specificity, especially in target tissues of the lung/bronchial tract. For these tissues the expression of CLDN18.1 was reported. To analyze whether the diagnostic antibody cross reacts with the lung/bronchial expressed isoform of CLDN18.1 all available lung/bronchial tissues were screened. No signals were detected with lung and bronchial tissues; see Table 7, below. The CLDN18 isoform expressed in these respiratory tissues is not recognized by the antibody 43-14A.

Example 7: Epitope Mapping of the mumAbs 43-14A and 35-22A

Peptide ELISA was performed to identify the antibody-binding epitopes on CLDN18.2. Each purified antibody was tested on overlapping peptides covering the C-terminal sequence of CLDN18.2. 35-22A and 43-14A both showed specific binding to an epitope mapping to the peptide TEDEVQSYPSKHDYV. The following sequence was determined as the reactive sequence: EVQSYPSKHDYV.

Example 8: Sequence Analysis of the mumAbs 43-14A and 35-22A

An analysis of the sequence of the antibodies 43-14A and 35-22A is shown in FIG. 3.

Example 9: Staining of Different Cancer Tissues

Immunohistochemistry (IHC) was performed on slides of 4% buffered formalin fixed paraffin embedded samples. Paraffin embedding was performed according to standard protocols.

After deparaffinization, all slides were subjected to antigen retrieval by boiling in 10 mM citric acid supplemented with 0.05% Tween-20 (pH 6.0) at 120° C. for 10 min, subsequently quenched (by 2% H2O2) blocked and incubated overnight at 4° C. with 0.2 to 0.5 µg/ml diagnostic monoclonal mouse anti-CLNDN18.2 antibody 43-14A or 35-22A. Antibody binding was visualized with horseradish-peroxidase-labeled secondary antibodies using the polymer-based Powervision antibody (Power Vision HRP goat-a-mouse; Immunologic, Duiven, The Netherlands) and a substrate-chromogen solution (VectorRed; Vector Labs, Burlingame, USA). Sections were subsequently counter-stained with Mayer's haematoxylin (Carl Roth GmbH, Karlsruhe, Germany) and subjected to evaluation by the raters.

Histological Assessment

All samples were analyzed regarding the relative proportion of positive stained tumor cells in relation to all visible tumor cells for each section. The intensity of the staining was classified as negative (−), weakly positive (1+), medium positive (2+) and strongly positive (3+). Only membranous staining was considered as positive. Human stomach tissue served as positive control for each staining. Since PanIN (pancreatic intraepithelial neoplasia) are frequently found strong positive, those areas were also considered as internal staining intensity reference for strong positivity (3+).

Strong, membranous signals were generated by both antibodies in pancreatic, esophageal and stomach cancerous tissues (Table 8) or with antibody 43-14A in lung cancerous tissues (Table 9). The number of positive tumor cells varied interindividually between the different tumor cases. The biggest part of the analysed samples was 2+ to 3+ positive.

TABLE 1

| | | | | | | Immunization schemes for antibodies | | | | | |
|---|---|---|---|---|---|---|---|---|---|---|---|
| | | | | Mouse | Antigen | | | Adjuvant | | Administration | |
| Date | Day | Event | Strain | ID | [µl] | [µg] | Code | [µl]/[µg] | Code | Route | Volume |
| | | | | Mouse 5 Immunization #20 - Fusion 35 | | | | | | | |
| 27. Oct. 2010 | 0 | 1. Immunization | C57BL/6 | M5 | 100 | 100 | C-terminal GC182-HIS | 100 | Gerbu MM | i.p. | 200 µl |
| 4. Nov. 2010 | 7 | 2. Immunization | C57BL/6 | M5 | 100 | 100 | C-terminal GC182-HIS | 50/50 | CpG-PTO | i.p. | 200 µl |
| 10. Nov. 2010 | 14 | 3. Immunization | C57BL/6 | M5 | 100 | 100 | C-terminal GC182-HIS | 100 | Gerbu MM | i.p. | 200 µl |
| 17. Nov. 2010 | 21 | 4. Immunization | C57BL/6 | M5 | 100 | 100 | C-terminal GC182-HIS | 100 | Gerbu MM | i.p. | 200 µl |
| 24. Nov. 2010 | 28 | Boost | C57BL/6 | M5 | 100 | 100 | C-terminal GC182-HIS | 100 | Gerbu MM | i.p. | 200 µl |
| 26. Nov. 2010 | 30 | Fusion #35 | C57BL/6 | M5 | | | | | | | |
| | | | | Mouse 4 Immunization #20 - Fusion 43 | | | | | | | |
| 27. Oct. 2010 | 0 | 1. Immunization | BALB/c | M4 | 100 | 100 | C-terminal GC182-HIS | 100 | Gerbu MM | i.p. | 200 µl |

TABLE 1-continued

Immunization schemes for antibodies

| Date | Day | Event | Strain | Mouse ID | Antigen [μl] | Antigen [μg] | Antigen Code | Adjuvant [μl]/[μg] | Adjuvant Code | Administration Route | Administration Volume |
|---|---|---|---|---|---|---|---|---|---|---|---|
| 10. Nov. 2010 | 14 | 2. Immunization | BALB/c | M4 | 100 | 100 | C-terminal GC182-HIS | 100 | Gerbu MM | i.p. | 200 μl |
| 17. Nov. 2010 | 21 | 3. Immunization | BALB/c | M4 | 100 | 100 | C-terminal GC182-HIS | 100 | Gerbu MM | i.p. | 200 μl |
| 24. Nov. 2010 | 28 | 4. Immunization | BALB/c | M4 | 100 | 100 | C-terminal GC182-HIS | 100 | Gerbu MM | i.p. | 200 μl |
| 8. Dec. 2010 | 42 | 5. Immunization | BALB/c | M4 | 100 | 100 | C-terminal GC182-HIS | 100 | Gerbu MM | i.p. | 200 μl |
| 22. Dec. 2010 | 56 | 6. Immunization | BALB/c | M4 | 100 | 100 | C-terminal GC182-HIS | 100 | Gerbu MM | i.p. | 200 μl |
| 5. Jan. 2011 | 70 | 7. Immunization | BALB/c | M4 | 100 | 100 | C-terminal GC182-HIS | 100 | Gerbu MM | i.p. | 200 μl |
| 12. Jan. 2011 | 77 | Boost | BALB/c | M4 | 100 | 100 | C-terminal GC182-HIS | 100 | Gerbu MM | i.p. | 200 μl |
| 14. Jan. 2011 | 79 | Fusion #43 | BALB/c | M4 | | | | | | | |

TABLE 2 mumAbs positive selected by Western Blot analysis

| slide number | Tissue | Antibody | Antibody conc. | Cryo-/Paraffin | Mucosa epithelium | Subcellular pattern | % positive cells | bg on lamina propria | Lymphocytes | Vessels | smooth Musculature |
|---|---|---|---|---|---|---|---|---|---|---|---|
| 11_413 | human | 35-22A | 0.5 μg/ml | Paraffin | +++ | m | 90 | − | − | − | − |
| 11_910 | human | 43-14A | 0.2 μg/ml | Paraffin | +++ | m | 90 | − | − | − | − |

TABLE 3

Comparison of the two antibodies 35-22A and 43-14A on normal human stomach FFPE tissue

| Slide ID | Tissue detail | Antibody | Antibody conc. | development | Mucosa epithelium | Subcellular pattern | % positive cells | bg & cells in lamina propria | Lymphocytes | Fibrous tissue | Vessels | smooth Musculature | Comment |
|---|---|---|---|---|---|---|---|---|---|---|---|---|---|
| 11_413 | stomach 5 | 35-22A | 0.5 μg/ml | 1:30 min | +++ | m | 90 | − | − | − | − | − | very strong membranous staining of the mucosa epithelium, no bg on stroma, vessels and muscles |

The 43-14A wasn't tested at 0.5 μg/ml, because the 35-22A did already perform very well at 0.2 μg/ml and did serve as a rule.

| Slide ID | Tissue detail | Antibody | Antibody conc. | development | Mucosa epithelium | Subcellular pattern | % positive cells | bg & cells in lamina propria | Lymphocytes | Fibrous tissue | Vessels | smooth Musculature | Comment |
|---|---|---|---|---|---|---|---|---|---|---|---|---|---|
| 11_975 | stomach 1 | 35-22A | 0.1 μg/ml | 2:30 min | +++ | m | 90 | − | − | − | − | − | strong membranous staining of the mucosa epithelium, no bg on stroma, muscles, vessels or lamina propria |
| 11_975 | stomach 1 | 43-14A | 0.1 μg/ml | 2:30 min | +++ | m | 90 | − | − | − | − | − | strong membranous staining of the mucosa epithelium, no bg on stroma, muscles, vessels or lamina propria |
| 11_907 | stomach 5 | 35-22A | 0.2 μg/ml | 2:30 min | +++ | m | 90 | − | − | − | − | − | strong membranous staining of the mucosa epithelium, no bg on stroma, muscles, vessels or lamina propria |
| 11_910 | stomach 5 | 43-14A | 0.2 μg/ml | 2:30 min | +++ | m | 90 | − | − | − | − | − | strong membranous staining of the mucosa epithelium, no bg on stroma, muscles, vessels or lamina propria |

TABLE 4

Cancer tissue analysis - TMA127A

| slide number | Tissue detail | Tissue id | Antibody | Antibody conc. | Cryo-/Paraffin | development |
|---|---|---|---|---|---|---|
| 11_474 | Stomach CA (+++) | B04/01221 II | 35-22A | 0.1 µg/ml | Paraffin | 2:30 min |
| 11_474 | Stomach CA (++) | B06/09514 (5 | 35-22A | 0.1 µg/ml | Paraffin | 2:30 min |
| 11_474 | Stomach CA (+) | B05/09809 (4 | 35-22A | 0.1 µg/ml | Paraffin | 2:30 min |
| 11_474 | Renal CA | B08/13471 (3 | 35-22A | 0.1 µg/ml | Paraffin | 2:30 min |
| 11_475 | Stomach CA (+++) | B04/01221 II | 43-14A | 0.1 µg/ml | Paraffin | 2:30 min |
| 11_475 | Stomach CA (++) | B06/09514 (5 | 43-14A | 0.1 µg/ml | Paraffin | 2:30 min |
| 11_475 | Stomach CA (+) | B05/09809 (4 | 43-14A | 0.1 µg/ml | Paraffin | 2:30 min |
| 11_475 | Renal CA | B08/13471 (3 | 43-14A | 0.1 µg/ml | Paraffin | 2:30 min |

| slide number | Tumor cells | Subcellular pattern | % positive cells | Normal epithelial cells | Fibrous tissue | Vessels | smooth Musculature |
|---|---|---|---|---|---|---|---|
| 11_474 | ++/+++ | m | 90 | n.a. | – | – | – |
| 11_474 | (+)/+ | c/m | 10 | n.a. | – | – | – |
| 11_474 | – | n.a. | 0 | n.a. | – | – | – |
| 11_474 | – | n.a. | 0 | n.a. | – | – | n.a. |
| 11_475 | +++ | m | 90 | n.a. | – | – | – |
| 11_475 | (+)/+ | m/c | 10 | n.a. | – | – | – |
| 11_475 | – | – | 0 | n.a. | – | – | – |
| 11_475 | – | n.a. | 0 | n.a. | – | – | n.a. |

TABLE 5A

Normal tissue analysis

| slide number | Tissue | Tissue id | Antibody | Antibody conc. | Cryo-/Paraffin | development | Normal epithelial cells and functional tissue | Subcellular pattern | % positive cells | Lymphocytes | Fibrous tissue | Vessels | smooth Musculature | Fatty tissue |
|---|---|---|---|---|---|---|---|---|---|---|---|---|---|---|
| 11_577 | Stomach | Stomach 9 | 35-22A | 0.2 µg/ml | Paraffin | 00:50 | ++/+++ | m | 90 | – | – | – | – | n.a. |
| 11_1756 | Stomach | Stomach 9 | 43-14A | 0.2 µg/ml | Paraffin | 00:50 | +++ | m | >90 | – | – | – | – | n.a. |
| 11_580 | Colon | Colon 2 | 35-22A | 0.2 µg/ml | Paraffin | 02:15 | – | n.a. | n.a. | – | – | – | – | n.a. |
| 11_1753 | Colon | Colon 2 | 43-14A | 0.2 µg/ml | Paraffin | 02:15 | – | n.a. | n.a. | – | – | – | – | – |
| 11_586 | Kidney | Kidney 2 | 35-22A | 0.2 µg/ml | Paraffin | 02:15 | – | n.a. | n.a. | – | – | – | – | – |
| 11_1754 | Kidney | Kidney 2 | 43-14A | 0.2 µg/ml | Paraffin | 02:15 | – | n.a. | n.a. | n.a. | – | – | – | n.a. |
| 11_589 | Lung | Lung 2 | 35-22A | 0.2 µg/ml | Paraffin | 02:15 | – | n.a. | n.a. | – | – | – | – | n.a. |
| 11_1663 | Lung | Lung 2 | 43-14A | 0.2 µg/ml | Paraffin | 03:00 | – | n.a. | n.a. | – | – | – | – | n.a. |
| 11_595 | Pancreas | Pancreas 3 | 35-22A | 0.2 µg/ml | Paraffin | 02:15 | – | n.a. | n.a. | – | – | – | – | – |
| 11_1749 | Pancreas | Pancreas3 | 43-14A | 0.2 µg/ml | Paraffin | 02:15 | – | n.a. | n.a. | n.a. | – | – | – | – |
| 11_599 | Liver | Liver 1 | 35-22A | 0.2 µg/ml | Paraffin | 02:15 | – | n.a. | n.a. | – | – | – | – | – |
| 11_1751 | Liver | Liver 1 | 43-14A | 0.2 µg/ml | Paraffin | 02:15 | – | n.a. | n.a. | n.a. | – | – | – | – |

TABLE 5B

Normal tissue analysis - 43-14 A

| slide number | Tissue | Tissue id | Antibody | Antibody conc. | Cryo-/Paraffin | development | Normal epithelial cells and functional tissue | Subcellular pattern | % positive cells | Lymphocytes | Fibrous tissue | Vessels | smooth Musculature | Fatty tissue |
|---|---|---|---|---|---|---|---|---|---|---|---|---|---|---|
| 11_1748 | Pancreas | Pancreas 5 | 43-14A SF | 0.2 µg/ml | Paraffin | 02:15 | – | n.a. | n.a. | n.a. | – | – | – | – |
| 11_1750 | Liver | Liver 4.5 | 43-14A SF | 0.2 µg/ml | Paraffin | 02:15 | – | n.a. | n.a. | n.a. | – | – | – | – |
| 11_1755 | Kidney | Kidney 3 | 43-14A SF | 0.2 µg/ml | Paraffin | 02:15 | – | n.a. | n.a. | n.a. | – | – | – | – |
| 11_1757 | Stomach | Stomach 12 | 43-14A SF | 0.2 µg/ml | Paraffin | 02:15 | +++ | m | >90 | – | – | – | – | n.a. |
| 11_1758 | Heart | Heart 1 | 43-14A SF | 0.2 µg/ml | Paraffin | 02:15 | – | n.a. | n.a. | n.a. | – | – | – | – |
| 11_1759 | Heart | Heart 2 | 43-14A SF | 0.2 µg/ml | Paraffin | 02:15 | – | n.a. | n.a. | n.a. | – | – | – | – |

TABLE 6

Normal tissue analysis - One-Day-Protocol

| slide number | Tissue | Tissue id | Antibody | Antibody conc. | development | functional tissue | tumor tissue | Subcellular pattern | % positive cells | Lymphocytes | Fibrous tissue | Vessels | smooth Musculature | Fatty tissue |
|---|---|---|---|---|---|---|---|---|---|---|---|---|---|---|
| 11_2092 | Stomach | Stomach 9 | 43-14 A | 0.1 µg/ml | 03:30 | ++/+++ | n.a. | m | >90 | – | – | – | – | – |
| 11_2092 | Stomach | Stomach 9 | 35-22 A | 0.1 µg/ml | 03:30 | +/++ | n.a. | m | >90 | – | – | – | – | – |
| 11_2093 | Stomach | Stomach 9 | 43-14 A SF | 0.1 µg/ml | 03:30 | +++ | n.a. | m | >90 | – | – | – | – | – |
| 11_2093 | Stomach | Stomach 9 | 35-22 A SF | 0.1 µg/ml | 03:30 | + | n.a. | m | 70-80 | – | – | – | – | – |
| 11_2094 | TMA 127 A | TMA 127 A | 43-14 A | 0.1 µg/ml | 03:30 | n.a. | +/++ | m | 90 | – | – | – | n.a. | n.a. |
| 11_2094 | TMA 127 A | TMA 127 A | 35-22 A | 0.1 µg/ml | 03:30 | n.a. | + | m | <5 | – | – | – | n.a. | n.a. |
| 11_2095 | TMA 127 A | TMA 127 A | 43-14 A SF | 0.1 µg/ml | 03:30 | n.a. | +/++ | m | 90 | – | – | – | n.a. | n.a. |
| 11_2095 | TMA 127 A | TMA 127 A | 35-22 A SF | 0.1 µg/ml | 03:30 | n.a. | –/(+) | c | <5 | – | – | – | n.a. | n.a. |

TABLE 7

Analysis of normal respiratory tissues

| slide number | Tissue id | Antibody | Antibody conc. | Normal epithelial cells | Subcellular pattern | % positive cells | Lymphocytes | Fibrous tissue | Vessels | smooth Musculature |
|---|---|---|---|---|---|---|---|---|---|---|
| 11_1660 | lung 1 | muAb 43-14A | 0.2 µg/ml | – | – | – | n.a. | – | – | – |
| 11_1660 | lung 1 | muAb 43-14A | 0.5 µg/ml | – | – | – | n.a. | – | – | – |
| 11_1663 | lung 2 | muAb 43-14A | 0.2 µg/ml | – | – | – | – | – | – | – |
| 11_1663 | lung 2 | muAb 43-14A | 0.5 µg/ml | – | – | – | – | – | – | – |
| 11_1666 | lung 3 | muAb 43-14A | 0.2 µg/ml | – | – | – | – | – | – | – |
| 11_1666 | lung 3 | muAb 43-14A | 0.5 µg/ml | – | – | – | – | – | – | – |
| 11_1669 | lung 4 | muAb 43-14A | 0.2 µg/ml | – | – | – | – | – | – | – |
| 11_1669 | lung 4 | muAb 43-14A | 0.5 µg/ml | – | – | – | – | – | – | – |
| 11_1672 | lung 5 | muAb 43-14A | 0.2 µg/ml | – | – | – | – | – | – | – |
| 11_1672 | lung 5 | muAb 43-14A | 0.5 µg/ml | – | – | – | – | – | – | – |
| 11_1675 | bronchial | muAb 43-14A | 0.2 µg/ml | – | – | – | – | – | – | – |
| 11_1675 | bronchial | muAb 43-14A | 0.5 µg/ml | – | – | – | – | – | – | – |
| 11_1678 | bronchial | muAb 43-14A | 0.2 µg/ml | – | – | – | – | – | – | – |
| 11_1678 | bronchial | muAb 43-14A | 0.5 µg/ml | – | – | – | – | – | – | – |
| 11_1681 | bronchial | muAb 43-14A | 0.2 µg/ml | – | – | – | – | – | – | – |
| 11_1681 | bronchial | muAb 43-14A | 0.5 µg/ml | – | – | – | – | – | – | – |
| 11_1684 | stomach 9 | muAb 43-14A | 0.2 µg/ml | +++ | m | >90 | – | n.a. | – | – |

TABLE 8

Analysis of CLDN18.2 expression in esophageal, pancreatic and stomach cancerous tissues, using the monoclonal murine antibodies 43-14A and 35-22A

| Tissue ID | Ab | Tissue | Details Subtype | Tumor cells | % positive cells |
|---|---|---|---|---|---|
| H/2010/10869 IVG | 43-14A | pancreas CA | Acinar cell carcinoma | – | 0 |
| 1125005.22 | 43-14A | pancreas CA | Neuroendocrine carcinoma | ++ | 70 |
| H/2006/22797** IA | 43-14A | pancreas CA | Neuroendocrine carcinoma | – | 0 |
| B08/6284-VC | 35-22A | pancreas CA | Neuroendocrine carcinoma, NET G1 | – | 0 |
| B08/8549-4 | 35-22A | pancreas CA | Neuroendocrine carcinoma, NET G1 | – | 0 |
| B05/8523-3 | 35-22A | pancreas CA | PDAC | ++ | 1 |
| B06/16136-NP2 | 35-22A | pancreas CA | PDAC | ++ | 50 |
| B07/14168 | 35-22A | pancreas CA | PDAC | ++ | 80 |
| B07/14935 | 35-22A | pancreas CA | PDAC | – | 0 |
| B07/2633-III3 | 35-22A | pancreas CA | PDAC | +++ | 90 |
| B07/7430 | 35-22A | pancreas CA | PDAC | ++ | 90 |
| B08/5618-2 | 35-22A | pancreas CA | PDAC | +++ | 80 |
| B10/14198-VC | 35-22A | pancreas CA | PDAC | +++ | 80 |
| B10/706-VC3 | 35-22A | pancreas CA | PDAC | +++ | 60 |
| B11/2059-D | 35-22A | pancreas CA | PDAC | +++ | 80 |
| B11/4084 | 35-22A | pancreas CA | PDAC | +++ | 90 |
| 1125005.30 | 43-14A | pancreas CA | PDAC | – | 0 |
| 1125005.27 | 43-14A | pancreas CA | PDAC | ++ | 10 |
| 1125005.24 | 43-14A | pancreas CA | PDAC | ++ | 50 |
| 1125005.23 | 43-14A | pancreas CA | PDAC | ++ | 100 |
| 1125005.25 | 43-14A | pancreas CA | PDAC | +++ | 30 |
| 1125005.28 | 43-14A | pancreas CA | PDAC | +++ | 80 |

TABLE 8-continued

Analysis of CLDN18.2 expression in esophageal, pancreatic and stomach cancerous tissues, using the monoclonal murine antibodies 43-14A and 35-22A

| Tissue ID | Ab | Tissue | Details Subtype | Tumor cells | % positive cells |
|---|---|---|---|---|---|
| H/2008/13074 | 43-14A | pancreas CA | PDAC | +++ | 40 |
| H/2008/13194 | 43-14A | pancreas CA | PDAC | +++ | 50 |
| H/2008/380 | 43-14A | pancreas CA | PDAC | +++ | 90 |
| H/2009/11847 | 43-14A | pancreas CA | PDAC | +++ | 15 |
| H/2009/20336 | 43-14A | pancreas CA | PDAC | +++ | 90 |
| H/2009/23598 VII B | 43-14A | pancreas CA | PDAC | +++ | 40 |
| H/2010/11569 | 43-14A | pancreas CA | PDAC | +++ | 80 |
| H/2011/17191 VA | 43-14A | pancreas CA | PDAC | +++ | 60 |
| H/2009/4917 | 43-14A | pancreas CA | PDAC | +++ | 70 |
| H/2010/15941 | 43-14A | pancreas CA | PDAC | +++ | 50 |
| H/2010/6709 | 43-14A | pancreas CA | PDAC | +++ | 70 |
| 1125005.19 | 43-14A | esophagus CA | adenocarcinoma | ++ | 50 |
| B09/1491-III-2 | 43-14A | esophagus CA | adenocarcinoma | − | 0 |
| 06/14957-2 | 43-14A | esophagus CA | adenocarcinoma | ++ | 30 |
| 1125005.17 | 43-14A | esophagus CA | adenocarcinoma | +++ | 70 |
| 1083435B | 43-14A | esophagus CA | adenocarcinoma | ++ | 70 |
| 10b06684-II-3 | 43-14A | stomach CA | adenocarcinoma | +++ | 80 |
| 1125005.10 | 43-14A | stomach CA | adenocarcinoma | ++ | 30 |
| 1125005.6 | 43-14A | stomach CA | adenocarcinoma | ++ | 90 |

PDAC = pancreatic ductal adenocarcinoma

TABLE 9

Analysis of CLDN18.2 expression in lung cancerous tissues, using monoclonal murine antibody 43-14A

| | | | | Tumor cells | |
|---|---|---|---|---|---|
| B09/14758-3 | 0.2 µg/ml | bronchiolo-alveolar type | | − | — |
| B09/18323-IV5 | 0.2 µg/ml | bronchiolo-alveolar type | | − | — |
| B10/13211-VC4 | 0.2 µg/ml | bronchiolo-alveolar type | | +++ | 80% |
| B07/4771-3 | 0.2 µg/ml | carcinoid | | − | — |
| B07/5358 II2 | 0.2 µg/ml | carcinoid | | − | — |
| B08/3382-1 | 0.2 µg/ml | carcinoid | | − | — |
| B08/8898-II6 | 0.2 µg/ml | carcinoma, clear cell | | + | <1% |
| B09/12293 II2 | 0.2 µg/ml | carcinoma, spino cellular | | − | — |
| B06/12562-III3 | 0.2 µg/ml | Carcinoma, large cell | | − | — |
| B06/10820-II2 | 0.2 µg/ml | carcinoma, adeno | | − | — |
| B06/10876-2 | 0.2 µg/ml | carcinoma, adeno | | − | — |
| B06/16831-I3 | 0.2 µg/ml | carcinoma, adeno | | +++ | 80% |
| B07/03255 IV5 | 0.2 µg/ml | carcinoma, adeno | | +++ | 5% |
| B07/2296-3 | 0.2 µg/ml | carcinoma, adeno | | − | — |
| B07/709 II4 | 0.2 µg/ml | carcinoma, adeno | | ++ | <5% |
| B10/12713-II1 | 0.2 µg/ml | carcinoma, adeno | | ++ | <5% |
| B10/14197-2 | 0.2 µg/ml | carcinoma, adeno | | − | — |
| B10/16367-V2 | 0.2 µg/ml | carcinoma, adeno | | + | 1% |
| B09/1743 II3 | 0.2 µg/ml | carcinoma, adeno, squamous | | − | — |
| B09/17916-1 | 0.2 µg/ml | carcinoma, large cell | | − | — |
| B10/10814-3 | 0.2 µg/ml | carcinoma, large cell neuro endocrine | | + | 1% |
| B010/10646 | 0.2 µg/ml | carcinoma, squamous cell | | − | — |
| B06/3204-2 | 0.2 µg/ml | carcinoma, squamous cell | | − | — |
| B08/292-2 | 0.2 µg/ml | carcinoma, squamous cell | | ++ | <5% |
| B08/7434-IV | 0.2 µg/ml | carcinoma, squamous cell | | − | — |
| B09/45-2 | 0.2 µg/ml | carcinoma, squamous cell | | − | — |
| B10/10-2 | 0.2 µg/ml | carcinoma, squamous cell | | + | <1% |
| B10/11714 | 0.2 µg/ml | carcinoma, squamous cell | | − | — |
| B10/15779 | 0.2 µg/ml | carcinoma, squamous cell | | − | — |
| B10/17043 | 0.2 µg/ml | carcinoma, squamous cell | | − | — |
| B10/18106 | 0.2 µg/ml | carcinoma, squamous cell | | − | — |
| B07/6782-1 | 0.2 µg/ml | carcinoma; adeno, clear cell | | ++ | <1% |
| B07/9741-5 | 0.2 µg/ml | carcinoma; adeno, clear cell | | − | — |
| B08/16425-2 | 0.2 µg/ml | large cell neuro-endocrine | | ++ | <5% |
| B08/3019-V3 | 0.2 µg/ml | non-small cell CA | | − | — |
| B08/1099 V3 | 0.2 µg/ml | nt small cell long CA | | − | <1% |
| B08/12010-2 | 0.2 µg/ml | nt small cell long CA | | ++ | <1% |
| B10/17662-III3 | 0.2 µg/ml | small cell carcinoma | | − | — |

| Applicant's or agent's file reference 342-70 | International application No. |
|---|---|

INDICATIONS RELATING TO DEPOSITED MICROORGANISM OR OTHER BIOLOGICAL MATERIAL (PCT Rule 13bis)

A. The indications made below relate to the deposited microorganism or other biological material referred to in the description on page 4, line 32.

B. IDENTIFICATION OF DEPOSIT  Further deposits are identified on an additional sheet [X]

Name of depositary institution
DSMZ-Deutsche Sammlung von Mikroorganismen und Zellkulturen GmbH Address of depositary institution (including postal code and country)
Inhoffenstr. 7 B
38124 Braunschweig
DE

| Date of deposit | Accession Number |
|---|---|
| October 6, 2011 | DSM ACC3144 |

C. ADDITIONAL INDICATIONS (leave blank if not applicable)   This information is continued on an additional sheet [ ]

- Mouse (Mus musculus) myeloma Ag8.653 fused with mouse (Mus musculus) splenocytes
- Hybridoma secreting antibody against human CLDN18.2

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

| For receiving Office use only | For International Bureau use only |
|---|---|
| [ ] This sheet was received with the international application | [ ] This sheet was received by the International Bureau on: |
| Authorized officer | Authorized officer |

Form PCT/RO/134 (July 1998; reprint January 2004)

Additional Sheet for Biological Material

Identification of further deposits:

1) The Name and Address of depositary institution for the deposits are:

DSMZ-Deutsche Sammlung von Mikroorganismen und Zellkulturen GmbH
   Inhoffenstr. 7 B
   38124 Braunschweig
   DE

| Date of desposit | Accession Number | The indications made below relate to the deposited microorganism in the description on the following page(s) |
|---|---|---|
| October 6, 2011 | DSM ACC3143 | page 4, line 33 |

Additional Indications for all above mentioned deposits:

- Mouse (Mus musculus) myeloma Ag8.653 fused with mouse (Mus musculus) splenocytes
- Hybridoma secreting antibody against human CLDN18.2

2) Depositor:

All above mentioned depositions were made by:

Ganymed Pharmaceuticals AG
   Freiligrathstraße 12
   55131 Mainz
   DE

The invention claimed is:

1. An antibody or antigen binding fragment thereof that binds to claudin 18.2 (CLDN18.2) or a peptide having the amino acid sequence TEDEVQSYPSKHDYV (SEQ ID NO: 5) or EVQSYPSKHDYV (SEQ ID NO: 6) wherein the antibody or antigen-binding fragment comprises
   (i) an antibody heavy chain comprising:
      a CDR1 having the amino acid sequence set forth in SEQ ID NO: 8,
      a CDR2 having the amino acid sequence set forth in SEQ ID NO: 9, and
      a CDR3 having the amino acid sequence set forth in SEQ ID NO: 10; and
   an antibody light chain comprising:
      a CDR1 having the amino acid sequence set forth in SEQ ID NO: 12,
      a CDR2 having the amino acid sequence set forth in SEQ ID NO: 13, and
      a CDR3 having the amino acid sequence set forth in SEQ ID NO: 14; or
   (ii) an antibody heavy chain comprising:
      a CDR1 having the amino acid sequence set forth in SEQ ID NO: 16, a CDR2 having the amino acid sequence set forth in SEQ ID NO: 17, and
a CDR3 having the amino acid sequence set forth in SEQ ID NO: 18; and
an antibody light chain comprising:
a CDR1 having the amino acid sequence set forth in SEQ ID NO: 20,
a CDR2 having the amino acid sequence set forth in SEQ ID NO: 21, and
a CDR3 having the amino acid sequence set forth in SEQ ID NO: 22.

2. The antibody or antigen-binding fragment thereof of claim 1, wherein said CLDN18.2 is cell surface membrane-bound CLDN18.2.

3. The antibody or antigen-binding fragment thereof of claim 1, wherein said CLDN18.2 is present on cancer cells.

4. The antibody or antigen-binding fragment thereof of claim 3, wherein said cancer cells are CLDN18.2 expressing cancer cells.

5. The antibody or antigen-binding fragment thereof of claim 3, wherein said cancer cells are selected from the group consisting of gastric, esophageal, pancreatic, lung, ovarian, colon, hepatic, head-neck, and gallbladder cancer cells.

6. The antibody or antigen-binding fragment thereof of claim 1, wherein the antibody or antigen-binding fragment thereof does not bind to non-cancerous cells except stomach epithelial cells.

7. The antibody or antigen-binding fragment thereof of claim 1, wherein the antibody or antigen-binding fragment thereof does not bind to non-cancerous lung cells.

8. The antibody of claim 1, wherein the antibody is a chimeric, human or humanized antibody.

9. The antibody of claim 1, wherein the antibody is a monoclonal antibody.

10. A conjugate comprising an antibody or antigen-binding fragment of claim 1 coupled to at least one detectable label.

11. A hybridoma capable of producing the antibody of claim 1.

12. The antibody or antigen-binding fragment of claim 1, wherein said CLDN18.2 comprises the amino acid sequence according to SEQ ID NO: 2 of the sequence listing or a variant of said amino acid sequence.

13. The antibody or antigen-binding fragment of claim 1, wherein the antibody or antigen-binding fragment comprises
an antibody heavy chain comprising:
a CDR1 having the amino acid sequence set forth in SEQ ID NO: 16,
a CDR2 having the amino acid sequence set forth in SEQ ID NO: 17, and
a CDR3 having the amino acid sequence set forth in SEQ ID NO: 18; and
an antibody light chain comprising:
a CDR1 having the amino acid sequence set forth in SEQ ID NO: 20,
a CDR2 having the amino acid sequence set forth in SEQ ID NO: 21, and
a CDR3 having the amino acid sequence set forth in SEQ ID NO: 22.

14. The antibody or antigen-binding fragment of claim 1, wherein the antibody or antigen-binding fragment comprises
an antibody heavy chain comprising:
a CDR1 having the amino acid sequence set forth in SEQ ID NO: 8,
a CDR2 having the amino acid sequence set forth in SEQ ID NO: 9, and
a CDR3 having the amino acid sequence set forth in SEQ ID NO: 10; and
an antibody light chain comprising:
a CDR1 having the amino acid sequence set forth in SEQ ID NO: 12,
a CDR2 having the amino acid sequence set forth in SEQ ID NO: 13, and
a CDR3 having the amino acid sequence set forth in SEQ ID NO: 14.

15. The antibody or antigen-binding fragment of claim 13, wherein the antibody or antigen-binding fragment comprises an antibody heavy chain comprising the amino acid sequence set forth in SEQ ID NO: 15, and an antibody light chain comprising the amino acid sequence set forth in SEQ ID NO: 19.

16. The antibody or antigen-binding fragment of claim 14, wherein the antibody or antigen-binding fragment comprises an antibody heavy chain comprising the amino acid sequence set forth in SEQ ID NO: 7, and an antibody light chain comprising the amino acid sequence set forth in SEQ ID NO: 11.

17. A diagnostic test kit which comprises the antibody or antigen-binding fragment of claim 1.

18. A method for detecting CLDN18.2 or determining the quantity of CLDN18.2 in a sample comprising the steps of:
(i) contacting a sample with the antibody or antigen-binding fragment of claim 1 and
(ii) detecting the formation of a complex or determining the quantity of a complex between the antibody or the antigen-binding fragment and CLDN18.2.

19. A method for determining whether cells express CLDN18.2 comprising the steps of:
(i) contacting a cellular sample with the antibody or antigen-binding fragment of claim 1 and
(ii) detecting the formation of a complex between the antibody or the antigen-binding fragment and CLDN18.2 expressed by cells in said sample.

20. A method for diagnosis, detection or monitoring of cancer comprising the steps of:
contacting a biological sample with the antibody or antigen-binding fragment of claim 1 and
(ii) detecting the formation of a complex and/or determining the quantity of a complex between the antibody or the antigen-binding fragment and CLDN18.2.

21. A method for determining whether a cancer is treatable by a cancer therapy targeting CLDN18.2 comprising the steps of:
(i) contacting a sample comprising cancer cells with the antibody or antigen-binding fragment of claim 1 and
(ii) detecting the formation of a complex between the antibody or the antigen-binding fragment and CLDN18.2.

22. The method of claim 18, wherein the sample comprises a paraffin embedded tissue section fixed with paraformaldehyde.

23. The method of claim 18, wherein, in step (i), the antibody or antigen binding fragment is at a concentration of about 0.1 to about 0.5 µg/ml.

24. The method of claim 23, wherein the concentration is about 0.2 µg/ml.

25. The method of claim 18, wherein step (i) comprises incubating the sample with the antibody or antigen-binding fragment overnight at 4° C.

26. The method of claim 18, wherein the antibody or antigen binding fragment is labeled with a detectable label.

27. The method of claim 26, wherein the detectable label is an enzyme or a fluorophore.

28. The method of claim 18, wherein the method further comprises contacting the antibody or antigen-binding fragment with a secondary antibody, wherein the secondary antibody is labeled with a detectable label.

29. The method of claim 28, wherein the secondary antibody is a horseradish-peroxidase (HRP)-labeled secondary antibody.

30. The method of claim 29, wherein step (ii) comprises exposing the HRP-labeled secondary antibody to a chemiluminescent substrate.

31. The method of claim 18, wherein the antibody or antigen-binding fragment comprises
    an antibody heavy chain comprising:
        a CDR1 having the amino acid sequence set forth in SEQ ID NO: 8,
        a CDR2 having the amino acid sequence set forth in SEQ ID NO: 9, and
        a CDR3 having the amino acid sequence set forth in SEQ ID NO: 10; and
    an antibody light chain comprising:
        a CDR1 having the amino acid sequence set forth in SEQ ID NO: 12,
        a CDR2 having the amino acid sequence set forth in SEQ ID NO: 13, and
        a CDR3 having the amino acid sequence set forth in SEQ ID NO: 14.

32. The method of claim 18, wherein the antibody or antigen-binding fragment comprises an antibody heavy chain comprising the amino acid sequence set forth in SEQ ID NO: 7, and an antibody light chain comprising the amino acid sequence set forth in SEQ ID NO: 11.

33. The method of claim 18, wherein the antibody or antigen-binding fragment comprises
    an antibody heavy chain comprising:
        a CDR1 having the amino acid sequence set forth in SEQ ID NO: 16,
        a CDR2 having the amino acid sequence set forth in SEQ ID NO: 17, and
        a CDR3 having the amino acid sequence set forth in SEQ ID NO: 18; and
    an antibody light chain comprising:
        a CDR1 having the amino acid sequence set forth in SEQ ID NO: 20,
        a CDR2 having the amino acid sequence set forth in SEQ ID NO: 21, and
        a CDR3 having the amino acid sequence set forth in SEQ ID NO: 22.

34. The method of claim 18, wherein the antibody or antigen-binding fragment comprises an antibody heavy chain comprising the amino acid sequence set forth in SEQ ID NO: 15, and an antibody light chain comprising the amino acid sequence set forth in SEQ ID NO: 19.

* * * * *

SEQUENCE LISTING

<160> NUMBER OF SEQ ID NOS: 25

<210> SEQ ID NO 1
<211> LENGTH: 261
<212> TYPE: PRT
<213> ORGANISM: Homo sapiens

<400> SEQUENCE: 1

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 2
<211> LENGTH: 261
<212> TYPE: PRT
<213> ORGANISM: Homo sapiens

<400> SEQUENCE: 2

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg

```
        50                  55                  60
Gly Tyr Phe Thr Leu Leu Gly Leu Pro Ala Met Leu Gln Ala Val Arg
 65                  70                  75                  80

Ala Leu Met Ile Val Gly Ile Val Leu Gly Ala Ile Gly Leu Leu Val
                 85                  90                  95

Ser Ile Phe Ala Leu Lys Cys Ile Arg Ile Gly Ser Met Glu Asp Ser
                100                 105                 110

Ala Lys Ala Asn Met Thr Leu Thr Ser Gly Ile Met Phe Ile Val Ser
            115                 120                 125

Gly Leu Cys Ala Ile Ala Gly Val Ser Val Phe Ala Asn Met Leu Val
        130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
                180                 185                 190

Cys Ile Ala Cys Arg Gly Leu Ala Pro Glu Glu Thr Asn Tyr Lys Ala
            195                 200                 205

Val Ser Tyr His Ala Ser Gly His Ser Val Ala Tyr Lys Pro Gly Gly
        210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
                260

<210> SEQ ID NO 3
<211> LENGTH: 264
<212> TYPE: PRT
<213> ORGANISM: Mus musculus

<400> SEQUENCE: 3

Met Ser Val Thr Ala Cys Gln Gly Leu Gly Phe Val Val Ser Leu Ile
 1               5                  10                  15

Gly Phe Ala Gly Ile Ile Ala Ala Thr Cys Met Asp Gln Trp Ser Thr
                20                  25                  30

Gln Asp Leu Tyr Asn Asn Pro Val Thr Ala Val Phe Asn Tyr Gln Gly
            35                  40                  45

Leu Trp Arg Ser Cys Val Arg Glu Ser Ser Gly Phe Thr Glu Cys Arg
        50                  55                  60

Gly Tyr Phe Thr Leu Leu Gly Leu Pro Ala Met Leu Gln Ala Val Arg
 65                  70                  75                  80

Ala Leu Met Ile Val Gly Ile Val Leu Gly Val Ile Gly Ile Leu Val
                 85                  90                  95

Ser Ile Phe Ala Leu Lys Cys Ile Arg Ile Gly Ser Met Asp Asp Ser
                100                 105                 110

Ala Lys Ala Lys Met Thr Leu Thr Ser Gly Ile Leu Phe Ile Ile Ser
            115                 120                 125

Gly Ile Cys Ala Ile Ile Gly Val Ser Val Phe Ala Asn Met Leu Val
        130                 135                 140

Thr Asn Phe Trp Met Ser Thr Ala Asn Met Tyr Ser Gly Met Gly Gly
145                 150                 155                 160
```

```
Met Gly Gly Met Val Gln Thr Val Gln Thr Arg Tyr Thr Phe Gly Ala
                165                 170                 175

Ala Leu Phe Val Gly Trp Val Ala Gly Gly Leu Thr Leu Ile Gly Gly
            180                 185                 190

Val Met Met Cys Ile Ala Cys Arg Gly Leu Thr Pro Asp Asp Ser Asn
        195                 200                 205

Phe Lys Ala Val Ser Tyr His Ala Ser Gly Gln Asn Val Ala Tyr Arg
    210                 215                 220

Pro Gly Gly Phe Lys Ala Ser Thr Gly Phe Gly Ser Asn Thr Arg Asn
225                 230                 235                 240

Lys Lys Ile Tyr Asp Gly Gly Ala Arg Thr Glu Asp Asp Glu Gln Ser
                245                 250                 255

His Pro Thr Lys Tyr Asp Tyr Val
                260

<210> SEQ ID NO 4
<211> LENGTH: 261
<212> TYPE: PRT
<213> ORGANISM: Artificial Sequence
<220> FEATURE:
<223> OTHER INFORMATION: Consensus Sequence
<220> FEATURE:
<221> NAME/KEY: MISC_FEATURE
<222> LOCATION: (18)..(18)
<223> OTHER INFORMATION: Variable Amino Acid

<400> SEQUENCE: 4

Met Ser Val Thr Ala Cys Gln Gly Leu Gly Phe Val Val Ser Leu Ile
1               5                   10                  15

Gly Xaa Ala Gly Ile Ile Ala Ala Thr Cys Met Asp Gln Trp Ser Thr
                20                  25                  30

Gln Asp Leu Tyr Asn Asn Pro Val Thr Ala Val Phe Asn Tyr Gln Gly
            35                  40                  45

Leu Trp Arg Ser Cys Val Arg Glu Ser Ser Gly Phe Thr Glu Cys Arg
50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240
```

Tyr Asp Gly Gly Ala Arg Thr Glu Asp Glu Val Gln Ser Tyr Pro Ser
            245                 250                 255

Lys His Asp Tyr Val
        260

<210> SEQ ID NO 5
<211> LENGTH: 15
<212> TYPE: PRT
<213> ORGANISM: Artificial Sequence
<220> FEATURE:
<223> OTHER INFORMATION: Peptide For Immunization

<400> SEQUENCE: 5

Thr Glu Asp Glu Val Gln Ser Tyr Pro Ser Lys His Asp Tyr Val
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: Peptide For Immunization

<400> SEQUENCE: 6

Glu Val Gln Ser Tyr Pro Ser Lys His Asp Tyr Val
1               5                   10

<210> SEQ ID NO 7
<211> LENGTH: 134
<212> TYPE: PRT
<213> ORGANISM: Mus musculus

<400> SEQUENCE: 7

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Phe Gly Glu Thr Val Lys Ile Ser Cys Lys Ala Ser Gly Tyr Thr Phe
        35                  40                  45

Thr Asp Tyr Ser Ile His Trp Val Lys Gln Ala Pro Gly Lys Gly Leu
    50                  55                  60

Lys Trp Met Gly Trp Ile Asn Thr Glu Thr Gly Val Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Arg Thr Gly Phe Asp Tyr Trp Gly Gln Gly Thr
        115                 120                 125

Thr Leu Thr Val Ser Ser
    130

<210> SEQ ID NO 8
<211> LENGTH: 8
<212> TYPE: PRT
<213> ORGANISM: Mus musculus

<400> SEQUENCE: 8

Gly Tyr Thr Phe Thr Asp Tyr Ser
1               5

<210> SEQ ID NO 9
<211> LENGTH: 8
<212> TYPE: PRT
<213> ORGANISM: Mus musculus

<400> SEQUENCE: 9

Ile Asn Thr Glu Thr Gly Val Pro
1               5

<210> SEQ ID NO 10
<211> LENGTH: 8
<212> TYPE: PRT
<213> ORGANISM: Mus musculus

<400> SEQUENCE: 10

Ala Arg Arg Thr Gly Phe Asp Tyr
1               5

<210> SEQ ID NO 11
<211> LENGTH: 132
<212> TYPE: PRT
<213> ORGANISM: Mus musculus

<400> SEQUENCE: 11

Met Arg Phe Ser Ala Gln Leu Leu Gly Leu Leu Val Leu Trp Ile Pro
1               5                   10                  15

Gly Ser Thr Ala Asp Ile Val Met Thr Gln Ala Ala Phe Ser Ile Pro
            20                  25                  30

Val Thr Leu Gly Thr Ser Ala Ser Ile Ser Cys Arg Ser Ser Lys Asn
        35                  40                  45

Leu Leu His Ser Asp Gly Ile Thr Tyr Leu Tyr Trp Tyr Leu Gln Arg
    50                  55                  60

Pro Gly Gln Ser Pro Gln Leu Leu Ile Tyr Arg Val Ser Asn Leu Ala
65                  70                  75                  80

Ser Gly Val Pro Asn Arg Phe Ser Gly Ser Gly Ser Gly Thr Asp Phe
                85                  90                  95

Thr Leu Arg Ile Ser Arg Val Glu Ala Glu Asp Val Gly Val Tyr Tyr
            100                 105                 110

Cys Val Gln Val Leu Glu Leu Pro Phe Thr Phe Gly Gly Gly Thr Lys
        115                 120                 125

Leu Glu Ile Lys
    130

<210> SEQ ID NO 12
<211> LENGTH: 11
<212> TYPE: PRT
<213> ORGANISM: Mus musculus

<400> SEQUENCE: 12

Lys Asn Leu Leu His Ser Asp Gly Ile Thr Tyr
1               5                   10

<210> SEQ ID NO 13
<211> LENGTH: 3
<212> TYPE: PRT
<213> ORGANISM: Mus musculus

<400> SEQUENCE: 13

Arg Val Ser
1

```
<210> SEQ ID NO 14
<211> LENGTH: 9
<212> TYPE: PRT
<213> ORGANISM: Mus musculus

<400> SEQUENCE: 14

Val Gln Val Leu Glu Leu Pro Phe Thr
1               5

<210> SEQ ID NO 15
<211> LENGTH: 140
<212> TYPE: PRT
<213> ORGANISM: Mus musculus

<400> SEQUENCE: 15

Met Asn Phe Gly Leu Ser Leu Ile Phe Leu Val Leu Val Leu Lys Gly
1               5                   10                  15

Val Gln Cys Glu Val His Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Thr Pro Glu Lys Arg Leu
    50                  55                  60

Glu Trp Val Ala Thr Ile Ser Asp Gly Gly Ser Tyr Ser Tyr Tyr Pro
65                  70                  75                  80

Asp Asn Val Lys Gly Arg Phe Thr Ile Ser Arg Asp Asn Ala Lys Asn
                85                  90                  95

Asn Leu Tyr Leu Gln Met Ser His Leu Lys Ser Glu Asp Thr Ala Ile
            100                 105                 110

Tyr Tyr Cys Ala Arg Asp Ser Tyr Tyr Asp Asn Ser Tyr Val Arg Asp
        115                 120                 125

Tyr Trp Gly Gln Gly Thr Thr Leu Thr Val Ser Ser
    130                 135                 140

<210> SEQ ID NO 16
<211> LENGTH: 8
<212> TYPE: PRT
<213> ORGANISM: Mus musculus

<400> SEQUENCE: 16

Gly Phe Thr Phe Ser Ser Tyr Ala
1               5

<210> SEQ ID NO 17
<211> LENGTH: 8
<212> TYPE: PRT
<213> ORGANISM: Mus musculus

<400> SEQUENCE: 17

Ile Ser Asp Gly Gly Ser Tyr Ser
1               5

<210> SEQ ID NO 18
<211> LENGTH: 14
<212> TYPE: PRT
<213> ORGANISM: Mus musculus

<400> SEQUENCE: 18

Ala Arg Asp Ser Tyr Tyr Asp Asn Ser Tyr Val Arg Asp Tyr
1               5                   10
```

<210> SEQ ID NO 19
<211> LENGTH: 127
<212> TYPE: PRT
<213> ORGANISM: Mus musculus

<400> SEQUENCE: 19

Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Met Tyr
            20                  25                  30

Ala Ser Leu Gly Glu Arg Val Ser Ile Thr Cys Lys Ala Ser Gln Asp
        35                  40                  45

Ile Asn Thr Phe Leu Ser Trp Phe Gln Gln Lys Pro Gly Lys Ser Pro
    50                  55                  60

Lys Thr Leu Ile Tyr Arg Thr Asn Arg Leu Ile Asp Gly Val Pro Ser
65                  70                  75                  80

Arg Phe Ser Gly Ser Gly Ser Gly Gln Asp Tyr Ser Leu Thr Ile Ser
                85                  90                  95

Ser Leu Asp Tyr Glu Asp Met Gly Ile Tyr Tyr Cys Leu Gln Tyr Asp
            100                 105                 110

Glu Phe Pro Leu Thr Phe Gly Ala Gly Thr Lys Leu Glu Leu Lys
        115                 120                 125

<210> SEQ ID NO 20
<211> LENGTH: 6
<212> TYPE: PRT
<213> ORGANISM: Mus musculus

<400> SEQUENCE: 20

Gln Asp Ile Asn Thr Phe
1               5

<210> SEQ ID NO 21
<211> LENGTH: 3
<212> TYPE: PRT
<213> ORGANISM: Mus musculus

<400> SEQUENCE: 21

Arg Thr Asn
1

<210> SEQ ID NO 22
<211> LENGTH: 9
<212> TYPE: PRT
<213> ORGANISM: Mus musculus

<400> SEQUENCE: 22

Leu Gln Tyr Asp Glu Phe Pro Leu Thr
1               5

<210> SEQ ID NO 23
<211> LENGTH: 330
<212> TYPE: DNA
<213> ORGANISM: Artificial Sequence
<220> FEATURE:
<223> OTHER INFORMATION: Nucleic Acid Encoding Peptide For Immunization

<400> SEQUENCE: 23
atgcggggtt ctcatcatca tcatcatcat ggtatggcta gcatgactgg tggacagcaa    60
atgggtcggg atctgtacga cgatgacgat aaggatcgat ggggatccga gctcgagatg   120

```
atgtgcatcg cctgccgggg cctggcacca gaagaaacca actacaaagc cgtttcttat    180
catgcctcgg gccacagtgt tgcctacaag cctggaggct tcaaggccag cactggcttt    240
gggtccaaca ccaaaaacaa gaagatatac gatggaggtg cccgcacaga ggacgaggta    300
caatcttatc cttccaagca cgactatgtg                                     330
```

```
<210> SEQ ID NO 24
<211> LENGTH: 110
<212> TYPE: PRT
<213> ORGANISM: Artificial Sequence
<220> FEATURE:
<223> OTHER INFORMATION: Peptide For Immunization

<400> SEQUENCE: 24

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Arg Trp Gly Ser Glu Leu Glu Met Met Cys Ile Ala Cys Arg Gly Leu
            35                  40                  45

Ala Pro Glu Glu Thr Asn Tyr Lys Ala Val Ser Tyr His Ala Ser Gly
    50                  55                  60

His Ser Val Ala Tyr Lys Pro Gly Gly Phe Lys Ala Ser Thr Gly Phe
65                  70                  75                  80

Gly Ser Asn Thr Lys Asn Lys Lys Ile Tyr Asp Gly Gly Ala Arg Thr
                85                  90                  95

Glu Asp Glu Val Gln Ser Tyr Pro Ser Lys His Asp Tyr Val
            100                 105                 110

<210> SEQ ID NO 25
<211> LENGTH: 71
<212> TYPE: PRT
<213> ORGANISM: Artificial Sequence
<220> FEATURE:
<223> OTHER INFORMATION: Peptide For Immunization

<400> SEQUENCE: 25

Met Met Cys Ile Ala Cys Arg Gly Leu Ala Pro Glu Glu Thr Asn Tyr
1               5                   10                  15

Lys Ala Val Ser Tyr His Ala Ser Gly His Ser Val Ala Tyr Lys Pro
                20                  25                  30

Gly Gly Phe Lys Ala Ser Thr Gly Phe Gly Ser Asn Thr Lys Asn Lys
            35                  40                  45

Lys Ile Tyr Asp Gly Gly Ala Arg Thr Glu Asp Glu Val Gln Ser Tyr
    50                  55                  60

Pro Ser Lys His Asp Tyr Val
65                  70
```